(12) United States Patent
Smrdel et al.

(10) Patent No.: US 8,758,815 B2
(45) Date of Patent: Jun. 24, 2014

(54) PHARMACEUTICAL COMPOSITIONS COMPRISING A COMBINATION OF METFORMIN AND SITAGLIPTIN

(75) Inventors: Polona Smrdel, Ljubljana (SI); Tijana Stanic Ljubin, Ljubljana (SI); Luka Peternel, Ljubljana (SI); Uros Klancar, Ljubljana (SI)

(73) Assignee: Lek Pharmaceuticals D.D., Ljubjana (SI)

( * ) Notice: Subject to any disclaimer, the term of this patent is extended or adjusted under 35 U.S.C. 154(b) by 21 days.

(21) Appl. No.: 13/578,596

(22) PCT Filed: Feb. 9, 2011

(86) PCT No.: PCT/EP2011/051888
§ 371 (c)(1),
(2), (4) Date: Nov. 21, 2012

(87) PCT Pub. No.: WO2011/098483
PCT Pub. Date: Aug. 18, 2011

(65) Prior Publication Data
US 2013/0059002 A1    Mar. 7, 2013

(30) Foreign Application Priority Data
Feb. 10, 2010 (EP) .................................. 10153151

(51) Int. Cl.
*A61K 9/20* (2006.01)
*A61K 9/22* (2006.01)

(52) U.S. Cl.
USPC ........................................................ 424/464

(58) Field of Classification Search
None
See application file for complete search history.

(56) References Cited

FOREIGN PATENT DOCUMENTS

| WO | WO 2006/047248 A1 | 5/2006 |
|---|---|---|
| WO | WO 2009/121945 A2 | 10/2009 |
| WO | WO 2009121945 A2 * | 10/2009 |

OTHER PUBLICATIONS

Abdul et al., "A flexible technology for modified release of drugs: multi layered tablets", Journal of Controlled Release, vol. 97, No. 3, Jul. 7, 2004, pp. 393-405.

* cited by examiner

*Primary Examiner* — Anand Desai
*Assistant Examiner* — Melissa Mercier
(74) *Attorney, Agent, or Firm* — Arent Fox LLP

(57) ABSTRACT

The present invention relates to a pharmaceutical composition, preferably a pharmaceutical dosage form, comprising at least two separate compartments, wherein one compartment contains a composition comprising metformin or a pharmaceutically acceptable salt thereof and wherein another compartment contains a composition comprising sitagliptin.
The present invention also relates to a process for preparing dosage forms comprising metformin or a pharmaceutically acceptable salt thereof and sitagliptin or a pharmaceutically acceptable salt thereof, the process comprising the steps of:
a) providing one composition containing metformin or a pharmaceutically acceptable salt thereof and optionally also sitagliptin,
b) providing a further composition containing sitagliptin or a pharmaceutically acceptable salt thereof and optionally also metformin, and
c) combining the compositions to form compartments.
The present invention also refers to a process for preparing dosage forms comprising at least one compartment comprising metformin or a pharmaceutically acceptable salt thereof and sitagliptin or a pharmaceutically acceptable salt thereof, the process comprises providing a composition containing metformin or a pharmaceutically acceptable salt thereof, and sitagliptin or a pharmaceutically acceptable salt thereof, and a matrix agent.
Moreover, the present invention related to a dosage form obtained by said process, and to the use of said dosage form for the treatment of diabetes.

13 Claims, 7 Drawing Sheets

Percent sitagliptin dissolved from formulations described in Examples 1-4.

Figure 1: Percent sitagliptin dissolved from formulations described in Examples 1-4.
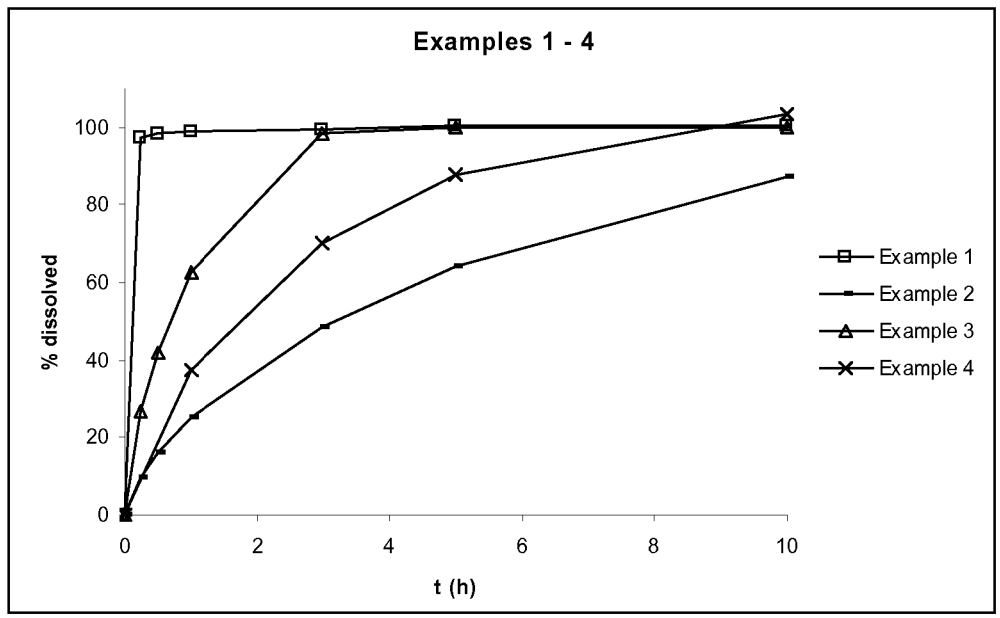
Figure 2: Percent metformin dissolved from formulations described in Examples 5-9.
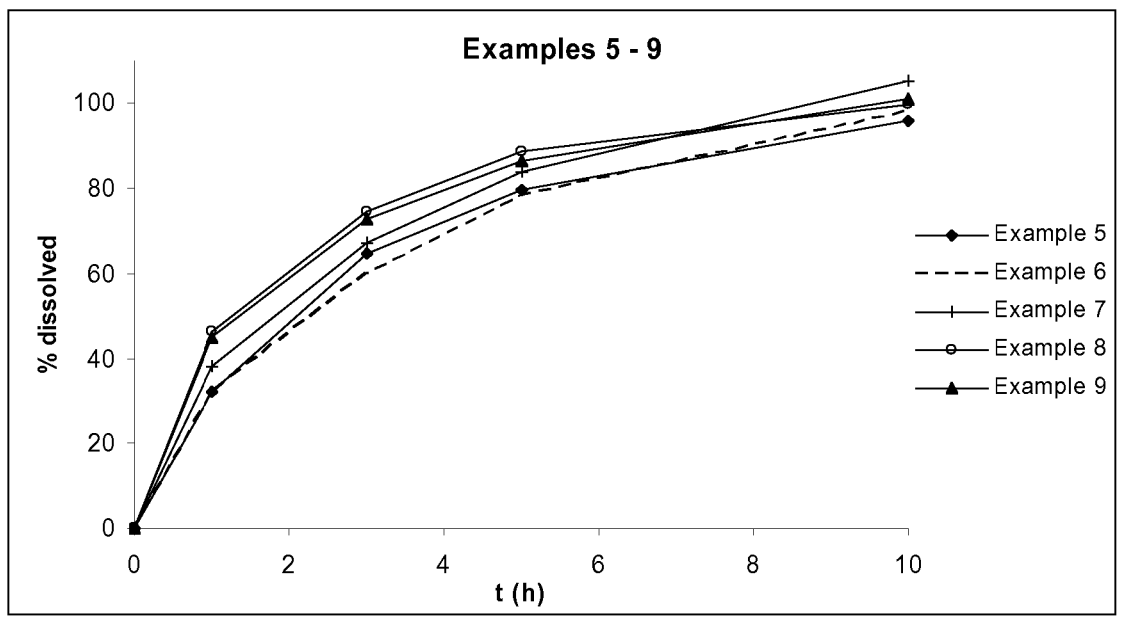

Figure 3: Percent sitagliptin and metformin dissolved from the formulation as described in Example 10.
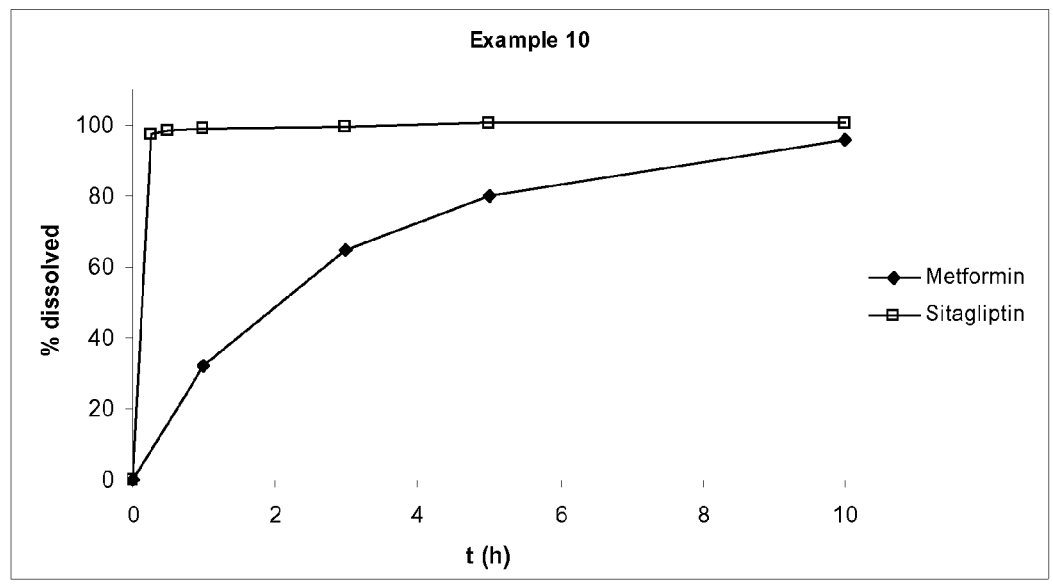
Figure 4: Percent sitagliptin and metformin dissolved from the formulation as described in Example 11.
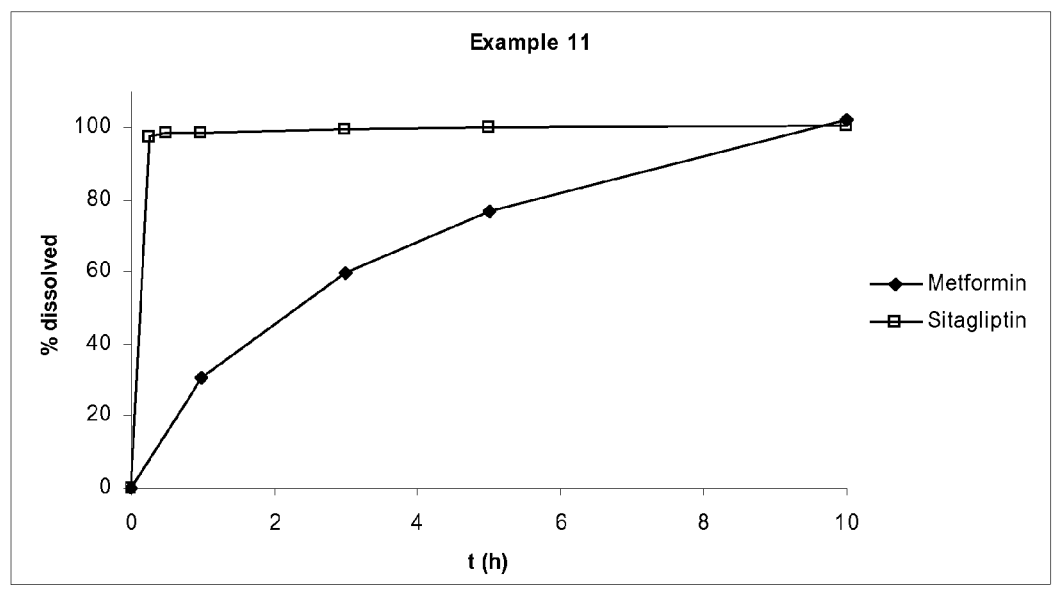

Figure 5: Percent sitagliptin and metformin dissolved from the formulation as described in Example 12.
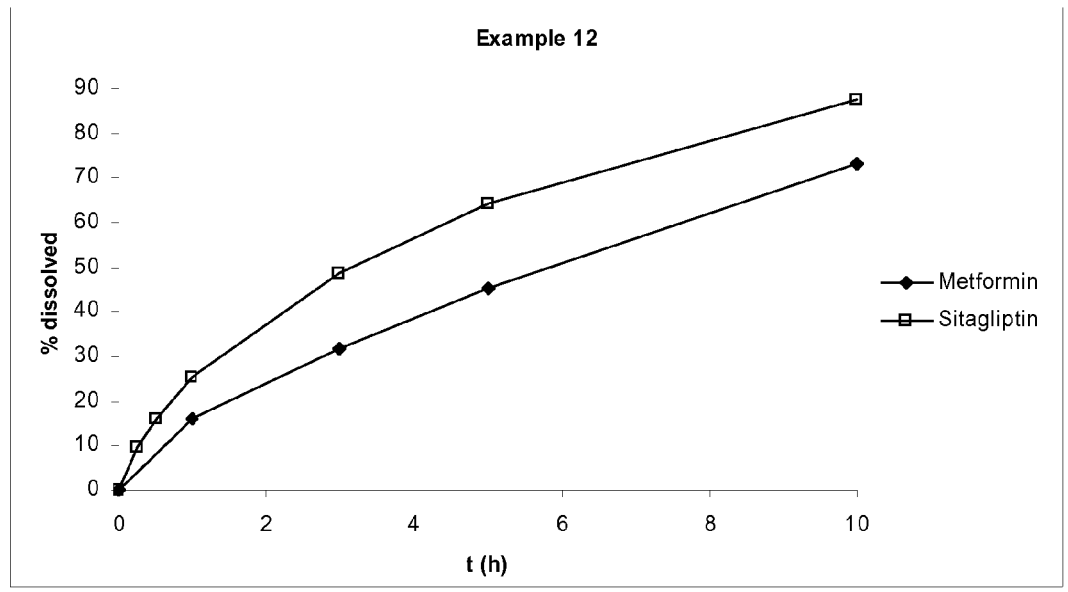
Figure 6: Percent sitagliptin and metformin dissolved from the formulation as described in Example 13.
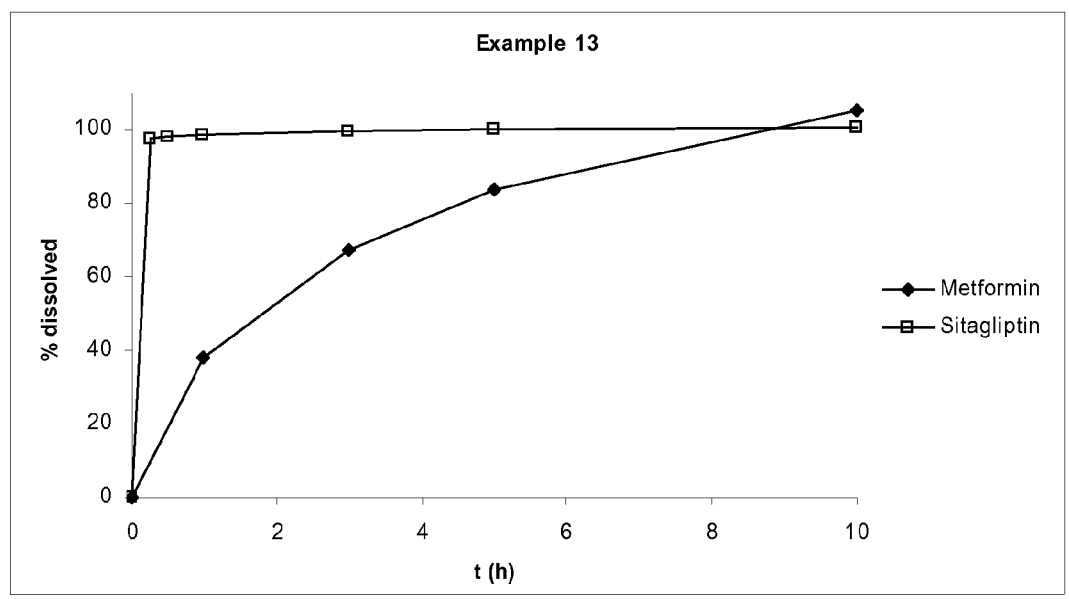

Figure 7: Percent sitagliptin and metformin dissolved from the formulation as described in Example 14.
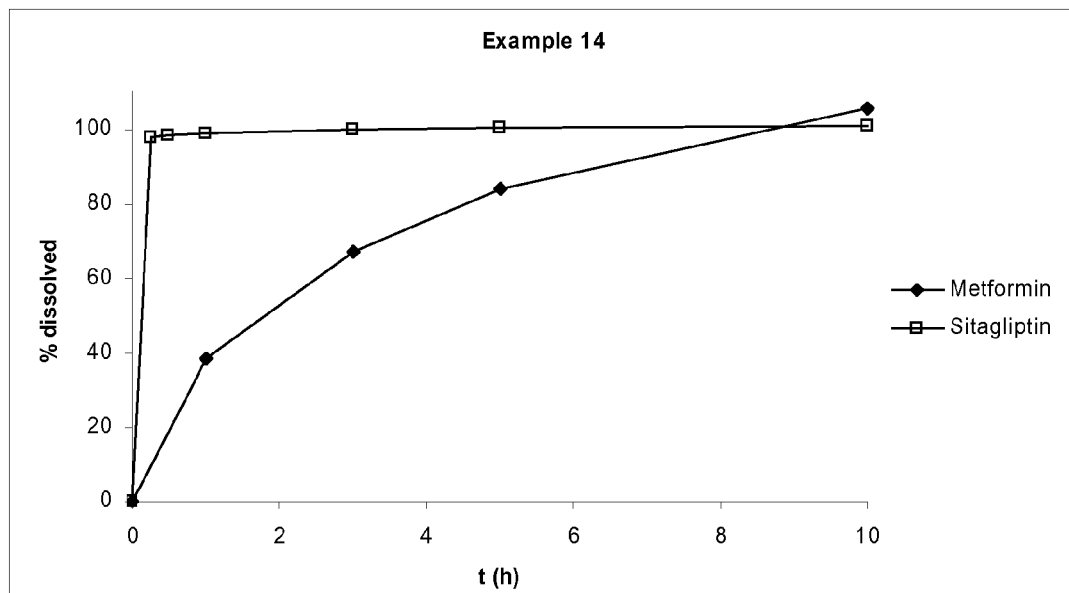
Figure 8: Percent sitagliptin and metformin dissolved from the formulation as described in Example 15.
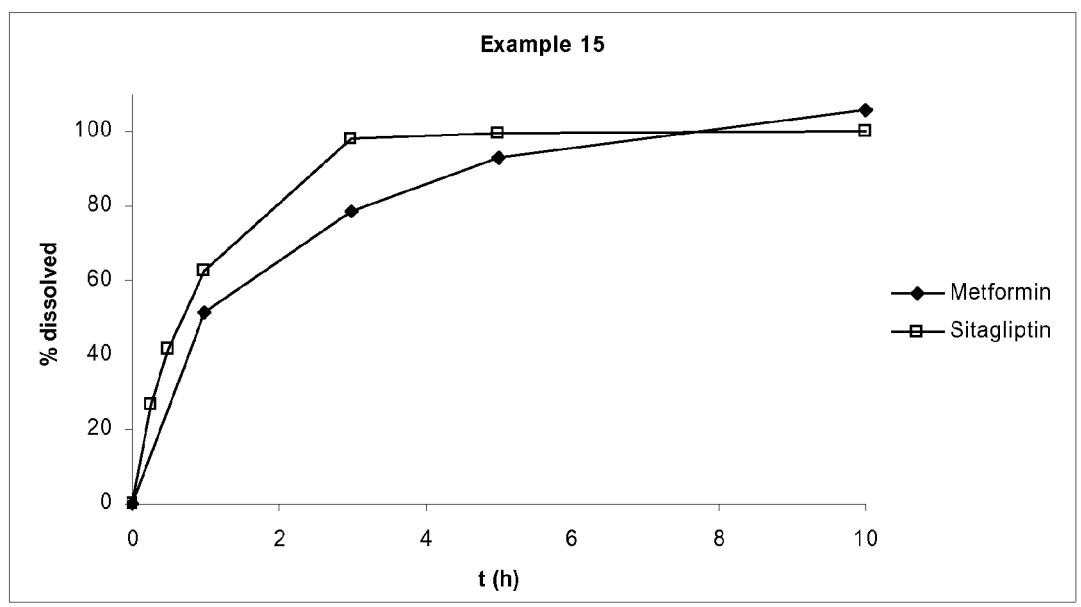

Figure 9: Percent sitagliptin and metformin dissolved from the formulation as described in Example 16.
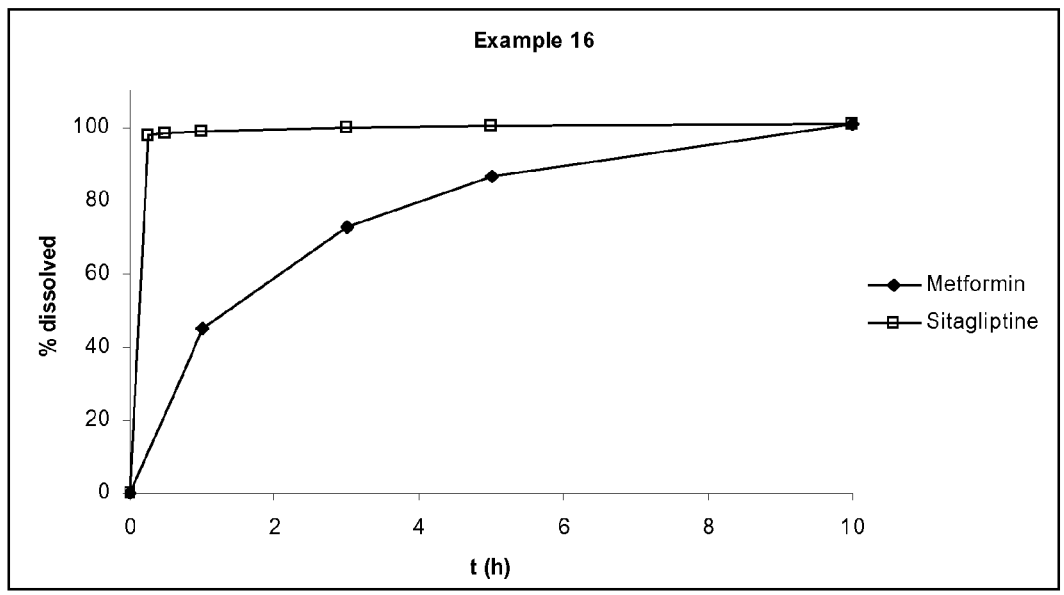
Figure 10: Percent sitagliptin and metformin dissolved from the formulation as described in Example 17.
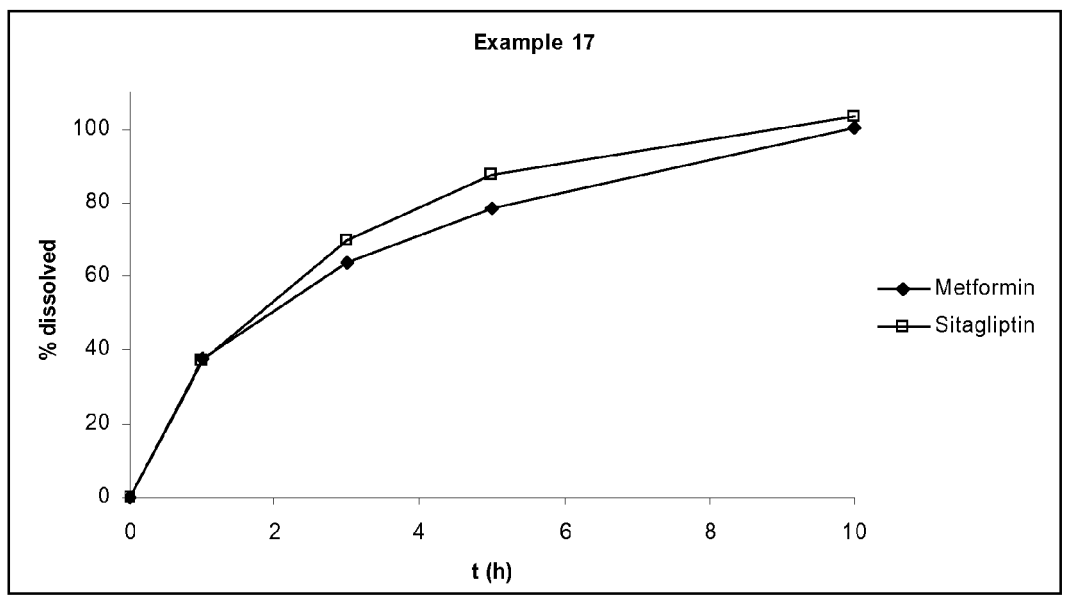

Figure 11: Percent sitagliptin and metformin dissolved from the formulation as described in Example 18.
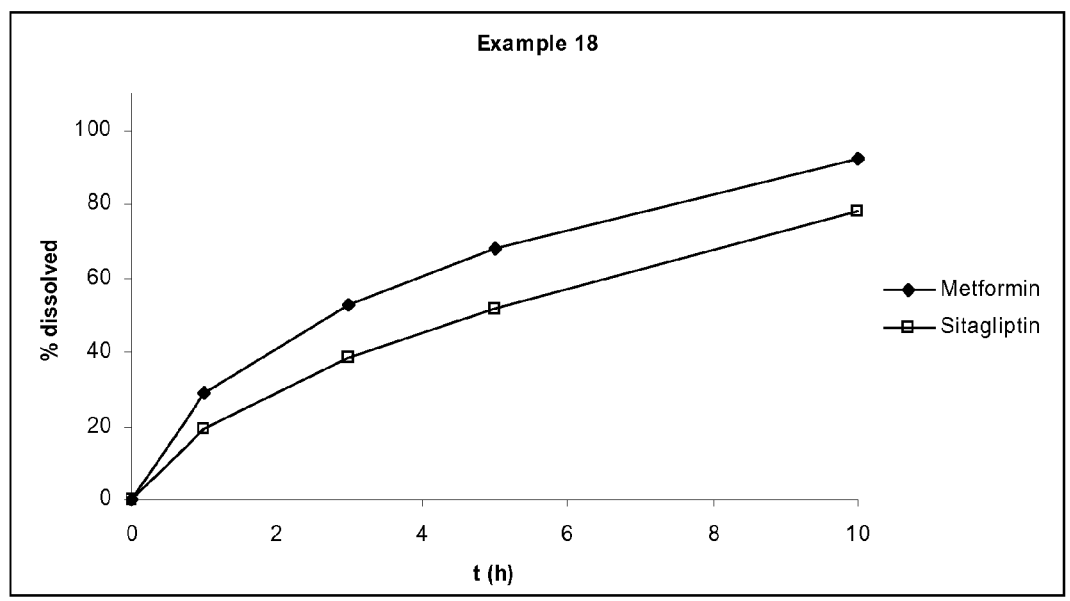
Figure 12: Percent sitagliptin and metformin dissolved from the formulation as described in Example 19.
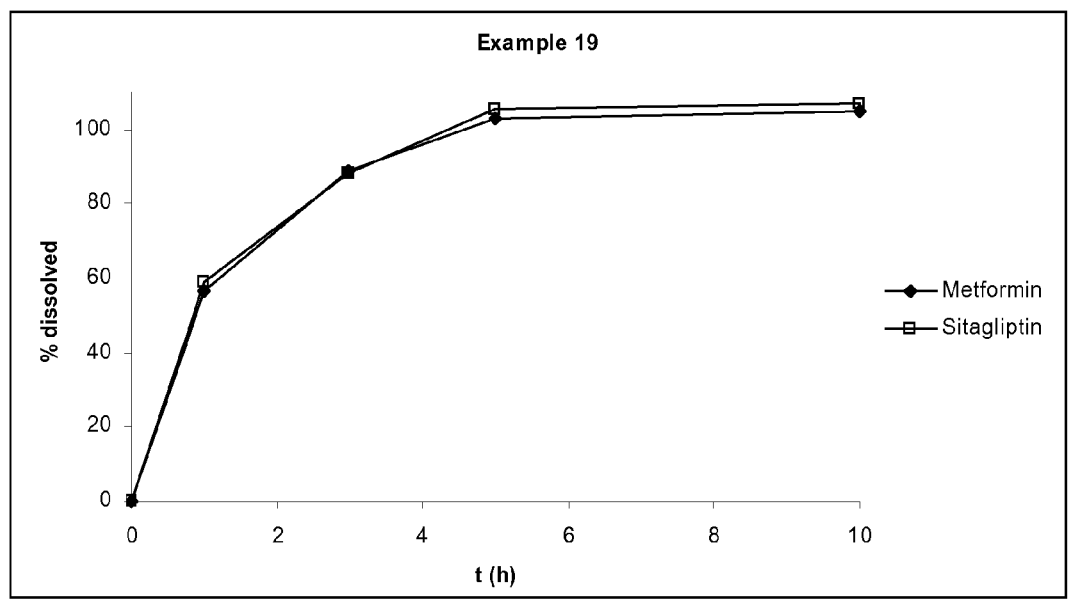

Figure 13: Percent sitagliptin and metformin dissolved from the formulation as described in Example 20.
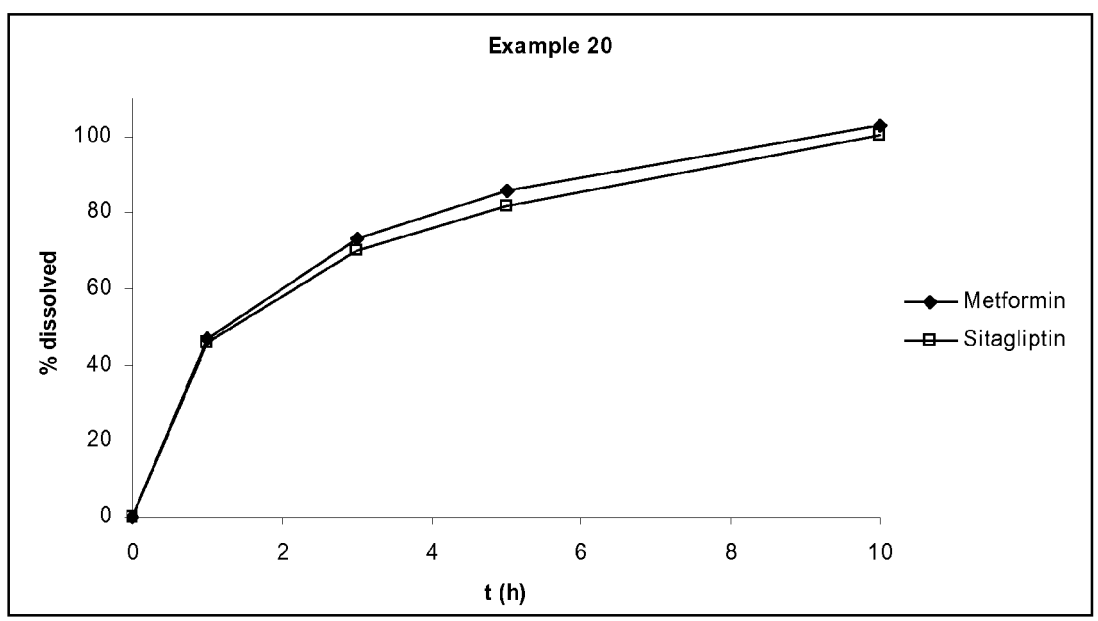

PHARMACEUTICAL COMPOSITIONS COMPRISING A COMBINATION OF METFORMIN AND SITAGLIPTIN

CROSS-REFERENCE TO RELATED APPLICATION

This application is a National Stage entry of International Application No. PCT/EP2011/051888, filed Feb. 9, 2011, which claims priority to European Application No. 10153151.5, filed Feb. 10, 2010, the entire specifications, claims and drawings of which are incorporated herewith by reference.

FIELD OF THE INVENTION

The present invention belongs to the field of pharmaceutical industry and relates to pharmaceutical compositions containing metformin or a pharmaceutically acceptable salt thereof and sitagliptin or a pharmaceutically acceptable salt thereof and a process for preparing such dosage forms, as well to dosage forms obtained by said process. Furthermore, the present invention relates to the use of said dosage form for the treatment of diabetes.

DESCRIPTION OF THE BACKGROUND ART

Sitagliptin is a potent, orally active dipeptidyl peptidase IV (DPP-IV) inhibitor used for the treatment of type II diabetes (Drugs of Today 2007; 43:801-814). There is a number of substrates beyond metabolic control that DPP-IV cleaves, and therefore inhibit their action, including hormones, neuropeptides, and chemokines. DPP-IV inhibitors prolong the action of hormone YY, neuropeptides such as substance P, and macrophage-derived chemokines. Potential adverse effects resulting from the prolongation of these messengers include inflammation (effect on substance P), increased blood pressure (effect on neuropeptide Y), and allergic reactions (effect on chemokines). Particularly, lower serum DPP-IV activity is related to depressive and anxiety symptoms and immune activation in patients with hepatitis C (Molecular Psychiatry 2001; 6:475-480) and to the neurogenic inflammation induced by substance P in chronic rhinosinusitis (The FASEB Journal 2002; 16:1132-1134). Furthermore, inhibition of DPP-IV may be a trigger of prostate cancer metastasis (Clin Exp Metastasis 2008; 25:765-776 and Int J Cancer 2004; 109:855-866) and inhibitors of DPP-IV have the potential to interfere with chemokine-mediated effects including but not limited to allergy (J Immunol 2008; 181:1120-1127).

A combination therapy of sitagliptin with the well established active ingredient of diabetes management metformin HCl provides even more effective treatment of type II diabetes (Drugs Today 2008; 44:303-314). Although metformin is effective at lowering blood glucose levels, its use is associated with gastrointestinal (GI) adverse effects, particularly diarrhea and nausea (Expert Opin Pharmacother 2006; 7:803-809). These adverse effects may limit the tolerated dose of metformin and cause patients to discontinue therapy.

Most currently available metformin formulations are immediate-release (IR) products, which release the entire drug within 1-2 h after dosing, resulting in high drug concentrations in the GI tract and consequently in undesired adverse effects.

WO 2009/111200 discloses pharmaceutical formulations comprising an inner core tablet composition comprising metformin hydrochloride. The inner core is coated with a sustained-release polymer and further comprises a coating comprising an immediate release composition of sitagliptin. When dissolving such tablets, firstly the sitagliptin from the immediate release coating is released. After dissolution of the immediate release coating, the sustained-release of the metformin hydrochloride starts.

EP 1 537 880 A1 discloses sustained release formulations of DPP-IV inhibitors in general, including sitagliptin. Such sustained release formulations comprise DPP-IV inhibitor and hydrophilic polymer.

WO 2009/099734 discloses pharmaceutical compositions providing an extended release of metformin and an immediate release of sitagliptin. The tablet core is comprised of metformin and an extended release excipient (HPMC). The tablet core is then coated with immediate release polymer comprising sitagliptin.

Although pharmaceutical compositions comprising metformin and sitagliptin exist, there is still a need for improved pharmaceutical compositions comprising metformin and sitagliptin as well as an improved process for preparing such preparations.

SUMMARY OF THE INVENTION

The present invention provides the following aspects, subject-matters and preferred embodiments, which respectively taken alone or in combination, further contribute to solving the object of the present invention:

(1) A pharmaceutical composition comprising at least two separate compartments, wherein one compartment contains a composition comprising metformin or a pharmaceutically acceptable salt thereof and wherein another compartment contains a composition comprising sitagliptin or a pharmaceutically acceptable salt thereof, wherein at least one of the compartments represents an extended release composition, wherein none of said two compartments represents a coating.

As described in further detail below, advantageously the pharmaceutical composition does not comprise a core which is coated with one or more coatings that contain an API such as metformin and/or sitagliptin.

The term "metformin" and "sitagliptin" denotes any pharmaceutical acceptable salts of metformin and sitagliptin. Within the meaning of the present invention, the term "metformin" preferably refers to the active pharmaceutical ingredient (API) "metformin hydrochloride (HCl)". Within the meaning of the present invention, the term "sitagliptin" preferably refers to the active pharmaceutical ingredient (API) "sitagliptin phosphate monohydrate". Within the context of the present specification, both metformin and sitagliptin are sometimes commonly referred to as "API".

Preferably, the compartments are in direct contact with each other (i.e. side by side compartments are formed) or the compartments are separated by a barrier such as an isolating layer.

(2) The pharmaceutical composition according to item (1), wherein each of the compartments constitutes a layer.

(3) The pharmaceutical composition according to item (1) or (2), wherein the pharmaceutical composition is a dosage form, preferably the dosage form is a tablet, preferably a multilayer tablet, further preferred a bilayer tablet or a trilayer tablet.

(4) The pharmaceutical composition according to any of items (1) to (3), wherein the other compartment also represents an extended release composition.

(5) The pharmaceutical composition according to item (1) or (2), wherein one compartment contains an extended release composition comprising metformin or a pharmaceutically acceptable salt thereof and another compartment contains an extended release or an immediate release composition comprising sitagliptin or a pharmaceutically acceptable salt thereof.

In a further preferred embodiment, one compartment contains an extended release composition comprising metformin or a pharmaceutically acceptable salt thereof and sitagliptin or a pharmaceutically acceptable salt thereof, and another compartment comprises an immediate release composition comprising sitagliptin or a pharmaceutically acceptable salt thereof or metformin or a pharmaceutically acceptable salt thereof.

In another preferred embodiment, one compartment contains an immediate release composition comprising metformin or a pharmaceutically acceptable salt thereof and, preferably, sitagliptin or a pharmaceutically acceptable salt thereof, and another compartment comprises an extended release composition comprising sitagliptin or a pharmaceutically acceptable salt thereof and/or metformin or a pharmaceutically acceptable salt thereof.

(6) The pharmaceutical composition according to any of the previous items, wherein the pharmaceutical composition, preferably the dosage form, comprises at least three compartments.

In a preferred embodiment, one compartment contains an immediate release composition comprising metformin or a pharmaceutically acceptable salt thereof and one compartment comprises an extended release composition comprising metformin or a pharmaceutically acceptable salt thereof and one compartment comprises an immediate or extended release composition comprising sitagliptin or a pharmaceutically acceptable salt thereof.

In a preferred embodiment, one compartment contains an immediate or extended release composition comprising metformin or a pharmaceutically acceptable salt thereof and one compartment comprises an extended release composition comprising sitagliptin or a pharmaceutically acceptable salt thereof and one compartment comprises an immediate release composition comprising sitagliptin or a pharmaceutically acceptable salt thereof.

(7) The pharmaceutical composition according to any of the previous items, wherein the extended release composition comprises at least one matrix agent selected from the group consisting of hydrophilic agents, lipophilic agents and inert matrix agents, wherein the hydrophilic matrix agents are selected from the group of pharmaceutical excipients which generate a gel in contact with water, including cellulose derivatives such as hydroxypropyl methyl cellulose, hydroxyethyl cellulose, hydroxypropyl cellulose, methyl cellulose and the like; noncellulose polysaccharides such as galactomannanes, guar gum, carob gum, gum arabicum, alginates, pectins, and the like; polyvinylpyrrolidone; polyvinylacetate polymers and copolymers; acrylic acid polymers and copolymers, polyethylene oxide and mixtures thereof;

the lipophilic matrix agents are selected from the group consisting of waxes such as white wax, bees wax, carnauba wax and the like; fatty acids and alcohols such as stearic acid, palmitic acid, lauric acid and the like, and cetyl alcohol, cetostearyl alcohol, stearyl alcohol and the like; fatty acids esters such as monostearates of propylene glycol and fatty acid esters of sucrose, sucrose distearate and the like; and glycerides such as mono-, di- or triglycerides, e.g. palmitin, stearin, behenic, laurin, myristin, hydrogenated vegetable, castor, cottonseed oils, glyceril behenate and the like; and mixtures thereof; and the inert matrix agents are selected from the group consisting of thermoplastic polymers, which are insoluble and indigestible in the gastrointestinal fluids, such as polyvinyl chloride, polyethylene, vinyl acetate/vinyl chloride copolymers, polymethylmethacrylates, polyam ides, silicones, ethyl cellulose, polystyrene, and mixtures thereof.

An extended release compartment according to the present invention which comprises at least one API, wherein preferably the API is sitagliptin or a pharmaceutically acceptable form thereof or metformin or a pharmaceutically acceptable salt thereof, is achieved by using a suitable dissolution rate controlling matrix forming agent (matrix agent) of hydrophilic, lipophilic or inert character, as described above, or a combination of several different matrix agents providing controlled release of the API.

(8) The pharmaceutical composition according to any of the previous items, wherein the immediate release composition does not comprise a matrix agent, in particular not a matrix agent as specified in item (7).

(9) The pharmaceutical composition according to any of the previous items, wherein the extended release tablet layer composition does not contain disintegrants and wherein the immediate release layer contains one or more disintegrants but no matrix forming agent. Preferably, the immediate release composition does not comprise a matrix agent, in particular not a matrix agent as specified in item (7).

The pharmaceutical composition according to the previous item, wherein the excipients are selected from the group consisting of binding agents, fillers, filler-binders, disintegrants, lubricants, sweeteners, glidants, flavourings and colouring agents, preferably the excipients are selected from the group consisting of binding agents, filler-binders, and lubricants. Preferably, the immediate release composition additionally comprises disintegrants.

Granulation liquids can be added especially if the composition comprises metformin or a pharmaceutically acceptable salt thereof, as also described elsewhere herein. Granulation liquid is removed during further processing of the respective compositions, however, some residual water is required in order that the granulate is compressible.

(10) The pharmaceutical composition, preferably the pharmaceutical dosage form, according to any one of the previous items, wherein the dosage form is a tablet composed of at least two compartments, preferably at least two layers. Preferably, the tablet comprises two or three layers.

(11) The pharmaceutical composition according to any of the preceding items, wherein an extended release compartment comprising metformin or a pharmaceutically acceptable salt thereof contains a matrix agent in an amount in the range of 10-40 wt.-%, preferably 15-40 wt.-%, and wherein an extended release compartment comprising sitagliptin or a pharmaceutically acceptable salt thereof contains a matrix agent in an amount in the range of 15-60 wt.-%, preferably 25-60 wt.-%.

In another embodiment of the invention, which can be combined with all embodiments as described herein, one of the at least two separate compartments comprises metformin as the only API. In this embodiment, the composition which comprises metformin as the only API represents an immediate or extended release composition.

If the APIs are contained in separate compartments, potential interactions between the APIs are avoided and the dissolution profile can be defined for each API independent from the dissolution profile of the other API. It has also been found that it is beneficial that the amount of matrix agent in extended release compartments comprising sitagliptin is higher than the amount of matrix agent in extended release compartments comprising metformin. Thus, if a pharmaceutical composition comprises two extended release compartments containing either sitagliptin or metformin, it is preferred that the amount of matrix agent is higher in the compartment containing sitagliptin. Furthermore, in order to keep the total weight of the pharmaceutical composition low, the amount of matrix agent(s) in extended release compartments comprising metformin should be as low as possible.

Preferably, the matrix agent is present in a composition (which represents a compartment), which comprises at least metformin (or a pharmaceutically acceptable salt thereof) or only metformin (or a pharmaceutically acceptable salt thereof) as the API, in an amount in the range of 10-40 wt.-%, further preferred in a range of 15-40 wt.-%, also preferred in a range of 15-35 wt.-%, further preferred in a range of 20-30 wt.-%. It is particularly advantageous to provide a composition comprising at least metformin or only metformin which contains the matrix agent in an amount of 20-30 wt.-%, if the pharmaceutical dosage form comprises metformin in an amount of at least 500 mg, further preferred at least 850 mg, most preferred at least 1000 mg.

Further preferred, the matrix agent is present in a composition (which represents a compartment), which comprises at least sitagliptin or a pharmaceutically acceptable salt thereof as the API or only sitagliptin or a pharmaceutically acceptable salt thereof as the API, in an amount in the range of 15-55 wt.-%, further preferred in the range of 30-55 wt.-%, further preferred in the range of 35-50 wt.-%, also preferred in the range of 35-47 wt.-%, further preferred in the range of 35-45 wt.-%.

(12) A pharmaceutical composition comprising at least one compartment, wherein the compartment contains an extended release composition comprising both metformin or a pharmaceutically acceptable salt thereof and sitagliptin or a pharmaceutically acceptable salt thereof and wherein the pharmaceutical composition comprises at least one matrix agent.

In a preferred embodiment, the amount of matrix agent(s) is in the range of 10-40 wt.-%, preferably in the range of 15-40 wt.-%, preferably in the range of 15-30 wt.-%, and more preferably in the range of 17-25 wt.-%, in particular in a pharmaceutical composition comprising one extended release composition.

In a further preferred embodiment, the matrix agent in the pharmaceutical composition comprising at least one extended release composition is at least one matrix agent selected from the group consisting of lipophilic and inert matrix agents (see item (7)). The matrix agent provides for extended release of both metformin and sitagliptin.

In a further preferred embodiment, the compartments according to item (12) do not represent a coating. With regard to the term "coating", reference is made to the explanation herein. Furthermore, as described in further detail elsewhere herein, advantageously the pharmaceutical composition does not comprise a core that is coated with one or more coatings that contain an API such as metformin and/or sitagliptin.

(13) The pharmaceutical composition, preferably the pharmaceutical dosage form, according to any of the previous items, wherein at least one, preferably at least two compartment(s) comprise(s) a matrix agent according to item (7).

(14) The pharmaceutical composition, preferably the pharmaceutical dosage form, according to any of the previous items, wherein fillers and/or filler-binder are selected from the group consisting of different grades of starches, such as maize starch, potato starch, rice starch, wheat starch, pregelatinized starch, fully pregelatinized starch, cellulose, such as microcrystalline cellulose or silicified microcrystalline cellulose, mannitol, erythritol, lactose, such as lactose monohydrate and lactose anhydrous, calcium salts, such as calcium hydrogenphosphate dihydrate, anhydrous dibasic calcium phosphate, sorbitol, and xylitol, particularly preferred, the fillers and/or filler-binders are selected from the group consisting of pregelatinized starch, microcrystalline cellulose, lactose monohydrate, and lactose, even further preferred the filler and/or filler-binder is selected from the group consisting of microcrystalline cellulose and anhydrous dibasic calcium phosphate;

For immediate release layers/compartments only (there is no need for disintegrants in extended release compartments), disintegrants are selected from the group consisting of carmellose calcium, carboxymethylstarch sodium, croscarmellose sodium, (cellulose carboxymethylether sodium salt, crosslinked), starch, such as sodium starch glycolate or corn starch, crosslinked polyvinylpyrrolidone (crospovidone), and low-substituted hydroxypropylcellulose, particularly preferred, the disintegrant is croscarmellose sodium; the lubricants are selected from the group consisting of stearic acid, talc, sodium stearyl fumarate and magnesium stearate, particularly preferred, the lubricant is magnesium stearate;

binding agents in compositions such as metformin comprising compositions are selected from the group consisting of polyvinyl pyrrolidone (Povidone), copolymers of vinylpyrrolidone with other vinylderivatives (Copovidone), hydroxypropyl methylcellulose, methylcellulose, hydroxypropylcellulose, powdered acacia, gelatin, guar gum, carbomer such as carbopol, polymethacrylates and starch, particularly preferred, the binding agents are selected from the group consisting of polyvinyl pyrrolidone and/or;

glidants are selected from the group consisting of colloidal silica, hydrophobic colloidal silica and magnesium trisilicate, such as talcum, particularly preferred the glidants are selected from the group consisting of colloidal silica and hydrophobic colloidal silica.

(15) The pharmaceutical composition according to any of the previous items, wherein the pharmaceutical composition is a dosage form that does not contain a significant amount of water or organic solvents that are added from external source. The term "does not contain a significant amount of water" means that the total amount of water in the pharmaceutical composition is less than 5 wt.-%, preferably less than 3 wt.-%, further preferred less than 2 wt.-% based on the total weight of the pharmaceutical composition.

In a preferred embodiment, the dosage form is a tablet, further preferred a multilayer tablet such as a bi- or a trilayer tablet.

(16) A process for preparing dosage forms comprising metformin or a pharmaceutically acceptable salt thereof and sitagliptin or a pharmaceutically acceptable salt thereof, the process comprising the steps of:

a) providing one composition containing metformin or a pharmaceutically acceptable salt and, optionally, also sitagliptin or a pharmaceutically acceptable salt, and b) providing a further composition containing sitagliptin or a pharmaceutically acceptable salt and, optionally, also metformin or a pharmaceutically acceptable salt, and c) combining the compositions to form compartments;

wherein at least one of the compartments represents an extended release composition, and wherein the compositions of step (a) and (b) are not applied in a coating process. Preferably, the compartments are combined so that they are in direct contact with each other (i.e. side by side compartments are formed) or so that they are separated by a barrier such as an isolating layer.

The terms "are in direct contact" and "side by side compartments are formed" mean that there is no barrier such as an isolating layer between the respective compartments. The term "isolating layer" within the meaning of the present invention denotes a layer that does not contain sitagliptin or a pharmaceutically acceptable salt thereof and metformin or a pharmaceutically acceptable salt thereof. Furthermore, this term also denotes a layer that is free of any API.

(17) The process according to item (16), wherein an extended release compartment comprising metformin or a pharmaceutically acceptable salt thereof is formed with a matrix agent in an amount in the range of 10-40 wt.-%, further preferred 15-40 wt.-%, and wherein an extended release compartment comprising sitagliptin or a pharmaceutically acceptable salt thereof is formed with a matrix agent in an amount in the range of 15-60 wt.-%, further preferred 25-60 wt.-%.

Further preferred ranges of the matrix agents in the respective extended release compartment are e.g. described above, see item (11).

(18) The process according to item (16) or (17), wherein each of the compartments constitutes a layer.

(19) The process according to any of items (16) to (18), wherein the dosage form is a tablet, preferably a bilayer or a trilayer tablet, which consists of two or three separate compartments, each of which constitutes a layer.

(20) The process according to any of items (16) to (19), wherein the preparation of the composition provided in step a) comprises a granulation step, and wherein the preparation of the composition of step b) comprises a mixing or granulation step depending on the API being present in the composition. In general, it is preferred that a granulation step is used if the composition comprises metformin. If the composition contains sitagliptin but no metformin, it is preferred to carry out a mixing step only.

In a further embodiment, the granulation step comprises a fluid bed granulation. This fluid bed granulation can be carried out with any suitable granulation liquid. In a preferred embodiment, the granulation liquid is demineralized water. In a further preferred embodiment, in step b) no granulation liquid is used if only mixing step is required. If metformin is introduced in this step, a granulation step is preferred.

(21) The process according to any of items (16) to (20), wherein process step c) involves the use of compression. Process step c) is preferably carried out in absence of any solvent added during process step c) The omitting of the use of solvents is potentially beneficial regarding the stability of sitagliptin, as there is no potential modification in polymorphism of the API and less potential chemical degradation of the API.

(22) The process according to the previous item, wherein the compositions which form the layers are compressed onto each other sequentially.

(23) The process according to any of items (16) to (22), wherein matrix agent(s) and optional one or more further excipients are incorporated in the respective compositions.

(24) The process according to any of the previous items, wherein the excipients are selected from the group consisting of binding agents, fillers, filler-binders, disintegrants, lubricants, glidants, flavourings and colouring agents; preferably the excipients are selected from the group consisting of binding agents, filler-binders, and lubricants; further preferred selected from the group consisting of binding agents, filler-binder, disintegrants, lubricants, and glidants.

Granulation liquid/s may have been incorporated, if at all and if desired, when the composition/s comprise/s metformin or a pharmaceutically acceptable salt thereof.

(25) The process according to item (23) or (24), wherein fillers and/or filler-binder are selected from the group consisting of different grades of starches, such as maize starch, potato starch, rice starch, wheat starch, pregelatinized starch, fully pregelatinized starch, cellulose, such as microcrystalline cellulose or silicified microcrystalline cellulose, mannitol, erythritol, lactose, such as lactose monohydrate and lactose anhydrous, calcium salts, such as calcium hydrogenphosphate, anhydrous dibasic calcium phosphate, sorbitol, and xylitol, particularly preferred, the fillers are selected from the group consisting of pregelatinized starch, microcrystalline cellulose, lactose monohydrate, and lactose, even further preferred the filler is selected from the group consisting of microcrystalline cellulose and anhydrous dibasic calcium phosphate;

the disintegrants are selected from the group consisting of carmellose calcium, carboxymethylstarch sodium, croscarmellose sodium, (cellulose carboxymethylether sodium salt, crosslinked), starch, such as sodium starch glycolate or corn starch, crosslinked polyvinylpyrrolidone (crospovidone), and low-substituted hydroxypropylcellulose, particularly preferred, the disintegrant (present only in immediate release compartment) is croscarmellose sodium;

the lubricants are selected from the group consisting of stearic acid, talc, sodium stearyl fumarate and magnesium stearate, particularly preferred, the lubricant is magnesium stearate;

binding agents, preferably used in metformin compartments, are selected from the group consisting of polyvinyl pyrrolidone (Povidone), copolymers of vinylpyrrolidone with other vinylderivatives (Copovidone), hydroxypropyl methylcellulose, methylcellulose, hydroxypropylcellulose, powdered acacia, gelatin, guar gum, carbomer such as carbopol, polymethacrylates and starch, particularly preferred, the binding agents are selected from the group consisting of polyvinyl pyrrolidone;

glidants are selected from the group consisting of colloidal silica, hydrophobic colloidal silica and magnesium trisilicate, such as talcum, particularly preferred the glidants are selected from the group consisting of colloidal silica and hydrophobic colloidal silica; and/or the sweeteners are selected from the group consisting of aspartame, saccharin sodium, dipotassium glycyrrhizinate, aspartame, stevia, thaumatin, and the like.

(26) A dosage form, obtained according to a process according to any of the previous items.

(27) The dosage form according to any of the preceding items for the manufacturing of a medicament for treatment of diabetes.

(28) A process for preparing dosage forms comprising at least one compartment comprising metformin or a pharmaceutically acceptable salt thereof and sitagliptin or a pharmaceutically acceptable salt thereof, the process comprises providing a composition containing metformin or a pharmaceutically acceptable salt thereof, and sitagliptin or a pharmaceutically acceptable salt thereof, and a matrix agent.

With regard to the dosage forms, compartments, API (e.g. the type of API, for example sitagliptin and metformin, and the amounts used), as well as with regard to the matrix agents (e.g. the type and/or amount of said agents used, reference is made to the indications throughout the whole specification.

In a further preferred embodiment, the compositions are not applied in a coating process. This means that neither of the compositions is applied onto the other composition, which e.g. forms a compartment, by using a coating process.

DETAILED DESCRIPTION OF THE INVENTION

The present invention is now described in more detail by preferred embodiments and examples, which are however presented for illustrative purpose only and shall not be understood as limiting the scope of the present invention in any way.

Although a sustained-release of metformin or metformin hydrochloride is beneficial, it is sometimes desired to have a pharmaceutical dosage form, wherein both APIs, metformin and sitagliptin, are simultaneously dissolved however independent from each other but not necessarily exhibiting the same dissolution profile, and not one after each other.

It has also been unexpectedly found that changes in polymorphism with respect to the APIs, in particular with respect to the API sitagliptin and pharmaceutically acceptable salts thereof, can be avoided if the use of any solvents like water or organic solvents is omitted. In particular, coating processes comprise the formation of compositions comprising the API such as sitagliptin in dissolved or suspended form. According to the invention, a pharmaceutical composition and dosage form has been devised which avoids the formation of API containing coating. Especially, omitting the use of solvents prevents any changes of the crystal form of the APIs which tend to be caused by dissolving the APIs when preparing solutions or suspensions containing the API(s). Thus, the pharmaceutical dosage forms according to the invention are in particular beneficial when using optionally polymorphs or pharmaceutically acceptable salts of the API(s). The maintenance of the respective polymorphs or salts provides for an improved reproducibility of the technological procedure.

Furthermore, it has been found that providing different compartments comprising APIs advantageously allows designing the most beneficial release profile for each compartment of the pharmaceutical composition. In particular, the present invention refers to multilayer tablets (e.g. two or more compartments that each form a layer), wherein the layers are placed upon each but do not represent tablets having a core having several layers around the core. When dissolving such multilayer tablets according to the invention, all layers at the same time are (or will become) in contact with the dissolution medium, whereas the tablets having an API-containing core with an API-containing layer around the core are dissolved layer by layer. As can be derived from the experiments as provided herein (compare FIGS. 1-13), the tablets according to the invention having at least two compartments provide a dissolution profile for the API(s) in each compartments without being significantly affected by the other compartment(s). By contrast, tablets containing an API-containing core and API-containing coatings around the core do not allow designing the dissolution profile of each coating layer without any influence of the outer coating layers. When dissolving such coated layers, inevitably the outer coating layer comprising one or more API(s) will firstly be dissolved and only after this, the inner coating layer(s) will be dissolved.

As to the dissolution profiles of the respective APIs being present in the respective compartment, extended-release formulations containing metformin and/or sitagliptin have several potential advantages over conventional immediate release (IR) tablets. First, the frequency of dosing can be reduced to once daily instead of two or three times daily, thereby avoiding unwanted side effects. The gradual release of metformin and/or sitagliptin into the gastrointestinal (GI) tract provides lower peak gastrointestinal concentrations, thus reducing the incidence of nausea and diarrhea. Additionally, a more uniform metformin and/or sitagliptin blood plasma levels is achieved by extended release metformin and/or sitagliptin formulations. These advantages contribute to improved patient adherence with metformin and/or sitagliptin therapy. Yet, the present invention allows releasing/dissolution profiles of metformin and sitagliptin independent from each other, which, in turn, allows for a well targeted and individually controlled release inter-play of the respective APIs: One sustained release API combined with the other sustained or immediate release API, as desired.

The present invention particularly provides for a very simple process for preparing pharmaceutical dosage forms wherein the compartments simultaneously start providing APIs in an immediate or extended release manner. For example, it is possible to provide one compartment with an immediate release of API, whereas the other compartment comprises an extended release composition. Such a mixed immediate/extended release dosage form is particularly advantageous if a part of one or both APIs has to be immediately dissolved and the extended release compartment should at the same time start to slowly release the API.

It has furthermore been found that improved pharmaceutical dosage forms comprising a combination of metformin and sitagliptin can be prepared by simple compression of blends containing the API(s) into tablets. Compared to prior art dosage forms like e.g. tablets comprising an API-containing coating, the inventive process is simpler, faster and cheaper. It is expected that the dosage forms according to the invention also provide for improved properties e.g. with respect to the dissolution profile and lower possibility for polymorphic changes. Without wishing to be bound by any theory, it is assumed that the dosage forms according to the invention have a lower time lag since all layers start to release simultaneously however independent from each other and not necessarily exhibiting the same dissolution profile. It is also expected that the dosage forms according to the invention possess an improved stability.

An additional benefit of the present invention is the possibility to combine both, an immediate and/or extended release compartment containing sitagliptin with an extended release compartment containing metformin in a very simple way, without significant influence on metformin dissolution, which is not possible if sitagliptin is applied as film coating on the core containing metformin. It is also possible to combine both, immediate and/or extended release layer of sitagliptin with immediate and/or extended release layer of metformin.

Thus, the present invention relates to a pharmaceutical composition, preferably a pharmaceutical dosage form, comprising at least two separate compartments, wherein one compartment contains a composition comprising metformin or a pharmaceutically acceptable salt thereof and wherein another compartment contains a composition comprising sitagliptin or a pharmaceutically acceptable salt thereof, wherein at least one of the compartments represents an extended release composition, and wherein none of said two compartments represents a coating.

The term "compartment" within the meaning of the present invention denotes a part of the dosage form comprising one or both pharmaceutically active ingredients (metformin and sitagliptin) and optional other active ingredients, optionally together with excipients as described elsewhere herein. Preferably, the compartments comprise a homogenous mixture of components. According to the present invention, the active ingredients are metformin and sitagliptin, or the respective pharmaceutically acceptable salts. Within the meaning of the present invention, the terms "metformin" and "sitagliptin" respectively include its pharmaceutically acceptable salts thereof. In each compartment, at least one type of active ingredient is contained. In one embodiment, at least in one, optionally in two compartments both metformin and sitagliptin are present. The compartments can comprise immediate or extended release compositions comprising the API(s).

According to the invention, at least one of the compartments comprises an extended release composition.

Preferably, the compartments are provided in the form of a layer. The pharmaceutical dosage form comprising the compartments will then represent monolayer tablets, bilayer tablets, trilayer tablets or multilayer tablets, preferably bilayer tablets. Thus, all compartments will be or will come in contact with body fluids at the same time, optionally after an outside coating that does not contain an API around the tablet is dissolved. Preferably, the dosage forms according to the present invention have at least two compartments, which are not in the form of a coating. This means that the two compartments which comprise metformin and/or sitagliptin do not represent layers which cover an object such as a core. However, it is not excluded that the final dosage form (which is administered to a person in need of) comprises a coating. For example, the final dosage form can comprise an outer coating. Such a coating (outer coating) does not contain the API being present in the dosage form. Such an outer coating can for instance be a film coating such as taste masking, aesthetic or functional coating or the like.

The term "composition" as used herein refers to the mixture of API(s) and optional one or more excipients which is comprised by the compartments. This means that the compartments consist of the compositions, wherein the term "compartment" denotes a spatial part of the pharmaceutical composition or dosage form and the term "composition" denotes the constituents of the compartment.

Preferably each of the at least two separate compartments, preferably two, respectively constitute a layer. Particularly preferred, according to the present invention, the dosage form is a tablet that consists of two or three separate compartments, each of which constitutes a layer.

The term "coating" as used herein refers to a layer which completely covers an object and is applied by film coating. By contrast, a compartment according to the invention can be in the form of a layer, wherein the layer can e.g. have the form of a disc and is applied by compaction.

Within the meaning of the present invention, the term "immediate release" denotes that within 2 hours, preferably within 1.5 h, more preferably within 1 h and most preferably within 30 minutes (min.), equal to or more than 80%, preferably equal to or more than 85%, even more preferably equal to or more than 90% of the API being present in the compartment is dissolved or released, respectively.

Furthermore, within the meaning of the present invention, the term "extended release" denotes that equal to or more than 95% of the API being present in the compartment are not dissolved or released, respectively, before 2 hours, more preferably not before 3 hours, more preferably not before 4 hours. A suitable test for determining the dissolution is the test using Apparatus 2 according to the US Pharmacopoeia 32-NF 27, described in General chapter 711 (Dissolution). Conditions chosen for the test were Apparatus 2 with 100 rpm in phosphate buffer medium pH 6.8.

Additionally preferred, sitagliptin is in crystalline form. Advantageously, sitagliptin can be used in one polymorphic form in the process for preparing the pharmaceutical compositions according to the invention. Especially, if the use of solvents is omitted, the obtained pharmaceutical compositions comprise sitagliptin in crystalline form, preferably in the same crystal form as was used as a starting material. The omitting of solvents prevents the crystalline sitagliptin to change its polymorphic form or turn into an amorphous form.

The preferred unit dosage strength of sitagliptin (free base anhydrate) for inclusion into a fixed dose combination dosage form (combination pharmaceutical formulation comprising both metformin and sitagliptin) of the present invention is, preferably, 25, 50 and 100 mg, equivalent to 32.125, 64.25 and 128.5 of sitagliptin phosphate monohydrate, respectively. Thus, the total amount of sitagliptin contained in the pharmaceutical composition or the pharmaceutical dosage form according to the invention is preferably between 10 mg and 150 mg, preferably between 20 and 110 mg. If pharmaceutical acceptable salts of sitagliptin are used, the amount of such salts to be present in the pharmaceutical composition or dosage form is calculated based on the amount of sitagliptin as defined above by considering the molecular weight of the pharmaceutically acceptable salt of sitagliptin and the molecular weight of sitagliptin.

The preferred unit dosage strength of metformin hydrochloride for inclusion into fixed dose combination dosage form (combination pharmaceutical formulation) of the present invention is preferably 500, 750, 850 and 1000 mg, representing the dosage strengths approved in the US for marketing to treat type II diabetes. Thus, the total amount of metformin hydrochloride contained in the pharmaceutical composition or the pharmaceutical dosage form according to the present invention is preferably between 400 mg and 1500 mg, preferably between 450 and 1100 mg. If other pharmaceutical acceptable salts than metformin hydrochloride are used, the amount of such salts to be present in the pharmaceutical composition or dosage form is calculated based on the amount of metformin hydrochloride as defined above by considering the molecular weight of the pharmaceutically acceptable salt of metformin and the molecular weight of metformin hydrochloride.

The present invention relates to the following preferred fixed-dose combinations of sitagliptin and metformin hydrochloride:

25 mg of sitagliptin and 500 mg of metformin HCl;
25 mg of sitagliptin and 750 mg of metformin HCl;
25 mg of sitagliptin and 850 mg of metformin HCl;
25 mg of sitagliptin and 1000 mg of metformin HCl;
50 mg of sitagliptin and 500 mg of metformin HCl;
50 mg of sitagliptin and 750 mg of metformin HCl;
50 mg of sitagliptin and 850 mg of metformin HCl;
50 mg of sitagliptin and 1000 mg of metformin HCl;
100 mg of sitagliptin and 500 mg of metformin HCl;
100 mg of sitagliptin and 750 mg of metformin HCl;
100 mg of sitagliptin and 850 mg of metformin HCl;
100 mg of sitagliptin and 1000 mg of metformin HCl.

The pharmaceutical composition according to the invention contains both metformin and sitagliptin. In a preferred embodiment of the invention, the pharmaceutical composition contains metformin and sitagliptin as the only APIs. As described above, the compartments of the pharmaceutical composition or dosage form according to the invention can comprise metformin and/or sitagliptin and, optionally, further API(s). The compartments can either represent immediate release compartments or extended release compartments. The compartments comprise a composition containing the API(s) and, optionally, one or more pharmaceutically acceptable excipients as described elsewhere herein.

In a preferred embodiment of the invention, the pharmaceutical composition/dosage form represents a bilayer tablet wherein the first layer of the bilayer tablet represents an extended release compartment comprising metformin or a pharmaceutically acceptable salt thereof and the second layer of the bilayer tablet represents an immediate release compartment comprising sitagliptin, or pharmaceutically acceptable salts thereof.

In another preferred embodiment of the invention, the pharmaceutical composition/dosage form represents a bilayer tablet wherein the first layer of the bilayer tablet represents an extended release compartment comprising metformin or a pharmaceutically acceptable salt thereof and the second layer of the bilayer tablet represents an extended release compartment comprising sitagliptin, or pharmaceutically acceptable salts thereof.

In another preferred embodiment of the invention, the pharmaceutical composition/dosage form represents a monolayer tablet wherein the monolayer represents an extended release compartment comprising metformin or a pharmaceutically acceptable salt thereof and sitagliptin, or a pharmaceutically acceptable salt thereof.

In another preferred embodiment of the invention, the pharmaceutical composition/dosage form represents a bilayer tablet wherein the first layer of the bilayer tablet represents an extended release compartment comprising metformin or a pharmaceutically acceptable salt thereof and sitagliptin, or pharmaceutically acceptable salt thereof, and the second layer of the bilayer tablet represents an immediate release compartment comprising sitagliptin, or pharmaceutically acceptable salt thereof.

In another preferred embodiment of the invention, the pharmaceutical composition/dosage form represents a bilayer tablet wherein the first layer of the bilayer tablet represents an extended release compartment comprising metformin or a pharmaceutically acceptable salt thereof and sitagliptin or pharmaceutically acceptable salt thereof, and the second layer of the bilayer tablet represents an immediate release compartment comprising metformin or a pharmaceutically acceptable salt thereof.

In another preferred embodiment of the invention, the pharmaceutical composition/dosage form represents a multilayer tablet, preferably a trilayer tablet, wherein the first layer of the trilayer tablet represents an immediate release compartment comprising metformin or a pharmaceutically acceptable salt thereof and the second layer represents an extended release compartment comprising metformin, or pharmaceutically acceptable salt thereof and the third layer of the trilayer tablet represents an immediate release compartment comprising sitagliptin, or pharmaceutically acceptable salt thereof.

In another preferred embodiment of the invention, the pharmaceutical composition/dosage form represents a multilayer tablet, preferably a trilayer tablet, wherein the first layer of the trilayer tablet represents an immediate release compartment comprising metformin or a pharmaceutically acceptable salt thereof and the second layer represents an extended release compartment comprising metformin, or pharmaceutically acceptable salt thereof and the third layer of the trilayer tablet represents an extended release compartment comprising sitagliptin, or pharmaceutically acceptable salt thereof.

In another preferred embodiment of the invention, the pharmaceutical composition/dosage form represents a multilayer tablet, preferably a trilayer tablet, wherein the first layer of the trilayer tablet represents an extended release compartment comprising metformin or a pharmaceutically acceptable salt thereof and the second layer represents an extended release compartment comprising sitagliptin, or pharmaceutically acceptable salt thereof and the third layer of the trilayer tablet represents an immediate release compartment comprising sitagliptin, or pharmaceutically acceptable salt thereof.

In another preferred embodiment of the invention, the pharmaceutical composition/dosage form represents a multilayer tablet, preferably a trilayer tablet, wherein the first layer of the trilayer tablet represents an immediate release compartment comprising metformin or a pharmaceutically acceptable salt thereof and the second layer represents an extended release compartment comprising sitagliptin, or pharmaceutically acceptable salt thereof and the third layer of the trilayer tablet represents an immediate release compartment comprising sitagliptin, or pharmaceutically acceptable salt thereof.

It is additionally preferred that an extended release compartment comprises a matrix agent (polymer) or a combination of several matrix agents (polymers). Further preferred, the extended release compartment comprises a composition comprising a matrix agent (matrix forming agent) of hydrophilic, lipophilic or inert character or a combination of several different matrix agents for providing a controlled release of the drug.

Preferably, the matrix agent is present in a extended release composition (which represents a compartment) comprising at least metformin or only metformin as the API in an amount in the range of 10-40 wt.-%, further preferred 15-40 wt.-%, further preferred in a range of 20-40 wt.-%, also preferred at least 20-35 wt.-%, also preferred in a range of 20 wt.-% to less than 35 wt.-%, further preferred 20-30 wt.-%. It is particularly advantageous to provide a composition comprising at least metformin or only metformin which contains the matrix agent in an amount of 20-30 wt.-%, if the pharmaceutical dosage form comprises metformin in an amount of at least 500 mg, further preferred at least 850 mg, most preferred at least 1000 mg. One reason for this is that the pharmaceutical dosage form becomes very big and less suitable for oral administration, in particular it is disadvantageous when administered to children.

Preferably, the matrix agent is present in an extended release composition (which represents a compartment) comprising at least sitagliptin or only sitagliptin as the API in an amount in the range of 15-60 wt.-%, further preferred in the range of 25-60 wt.-%, further preferred in the range of 30-60 wt.-%, further preferred in a range of 35-50 wt.-%, even further preferred in a range of 40-50 wt.-%. It has been found that when using a combination of metformin and sitagliptin in one pharmaceutical composition, it is advantageous to provide the aforementioned amounts of matrix agents in order to that the pharmaceutical composition can easily be swallowed.

Preferred matrix forming agents are polymers selected from the group consisting of hydrophilic, lipophilic and inert matrix agents, wherein
the hydrophilic matrix agents are selected from the group consisting of cellulose derivatives such as hydroxypropyl methyl cellulose, hydroxyethyl cellulose, hydroxypropyl cellulose, methyl cellulose and the like; noncellulose polysaccharides such as galactomannanes, guar gum, carob gum, gum arabicum, alginates, pectins, and the like; polyvinylpyrrolidone; polyvinylacetate polymers and copolymers; acrylic acid polymers and copolymers, polyethylene oxide and mixtures thereof;
the lipophilic matrix agents are selected from the group consisting of waxes such as white wax, bees wax, carnauba wax and the like; fatty acids and alcohols such as stearic acid, palmitic acid, lauric acid and the like, and cetyl alcohol, cetostearyl alcohol, stearyl alcohol and the like; fatty acids esters such as monostearates of propylene glycol and fatty acid esters of sucrose, sucrose distearate and the like; and glycerides such as mono-, di- or triglycerides, e.g. palmitin, stearin, behenic, laurin, myristin, hydrogenated vegetable, castor, cottonseed oils, glyceril behenate and the like; and mixtures thereof; and
the inert matrix agents are selected from the group consisting of thermoplastic polymers, which are insoluble and indigestible in the gastrointestinal fluids, such as polyvinyl chloride, polyethylene, vinyl acetate/vinyl chloride copolymers, polymethylmethacrylates, polyamides, silicones, ethyl cellulose, polystyrene, and the like.

Preferred hydrophilic matrix agents are selected from the group consisting of hydroxypropylmethylcellulose (Methocel, e.g. Methocel K100M Premium), hydroxypropyl cellulose, and polyethylene oxide (such as poliox WSR 303), preferred lipophilic matrix agents are selected from the group consisting of hydrogenated castor oil, and glyceril behenate, and preferred inert matrix agents are selected from the group consisting of ethylcellulose (such as ethylcellulose Ethocel, e.g. Ethocel 10 FT Premium), and polymethylmethacrylates (such as Eudragit® RS).

Two or more kinds of these polymers may be mixed at appropriate ratios for use.

Moreover, one or more pharmaceutically acceptable excipient/s can be added. Suitable pharmaceutically acceptable excipients that can be added to the compositions which form the compartments, include, but are not limited to, binding agents, fillers, filler-binder, disintegrants (for immediate release compartments), lubricants, sweeteners, glidants, flavourings and colouring agents. In a preferred embodiment, the excipients are selected from the group consisting of binding agents, fillers, filler-binders, disintegrants (for immediate release compartments), and lubricants. Optionally, in a further embodiment, the pharmaceutical composition additionally contains a granulation liquid. A granulation liquid may be used if a granulation step is carried out. In an embodiment of the present invention, a granulation step is comprised in the step of providing a composition comprising metformin or a pharmaceutically acceptable salt thereof.

In the following, preferred excipients are described which can be used in compositions which are either immediate release or extended release compositions. However, in case of immediate release compositions, preferably no excipients are added which provide for an extended release of the API(s), e.g. no excipients are used which are indicated above as suitable matrix agents (polymers). The excipients can also be used in an optional outer coating of the pharmaceutical composition, preferably of the dosage form. No disintegrants are present in extended release layers.

According to the present invention, any suitable filler and/or filler-binder can be used in the composition/s which form/s the compartment/s. Preferred fillers and/or filler-binder are selected from the group consisting of different grades of starches, such as maize starch, potato starch, rice starch, wheat starch, pregelatinized starch, fully pregelatinized starch, cellulose, such as microcrystalline cellulose or silicified microcrystalline cellulose, mannitol, erythritol, lactose, such as lactose monohydrate and lactose anhydrous, calcium salts (hydrogenphosphate), such as calcium hydrogenphosphate dihydrate, anhydrous dibasic calcium phosphate, sorbitol, and xylitol, particularly preferred, the fillers are selected from the group consisting of pregelatinized starch, microcrystalline cellulose, lactose monohydrate, and lactose, even further preferred the filler is selected from the group consisting of microcrystalline cellulose and anhydrous dibasic calcium phosphate.

According to the present invention, any suitable disintegrants can be used in the composition/s which form/s the immediate release compartment/s. Preferred disintegrants are selected from the group consisting of carmellose calcium, carboxymethylstarch sodium, croscarmellose sodium (cellulose carboxymethylether sodium salt, crosslinked), starch, such as sodium starch glycolate or corn starch, crosslinked polyvinylpyrrolidone (crospovidone), and low-substituted hydroxypropylcellulose; particularly preferred, the disintegrants are selected from the group consisting of croscarmellose sodium.

According to the present invention, any suitable lubricants can be used in the composition/s which form the compartment/s. Preferred lubricants are selected from the group consisting of stearic acid, talc, sodium stearyl fumarate and magnesium stearate, particularly preferred, the lubricant is magnesium stearate.

According to the present invention, any suitable binding agents for wet granulation can be used in the composition/s which form the metformin containing compartment/s. Preferred binding agents are selected from the group consisting of polyvinyl pyrrolidone (Povidone), copolymers of vinylpyrrolidone with other vinylderivatives (Copovidone), hydroxypropyl methylcellulose, methylcellulose, hydroxypropylcellulose, powdered acacia, gelatin, guar gum, carbomer such as carbopol, polymethacrylates and starch, particularly preferred binding agent is polyvinyl pyrrolidone.

According to the present invention, any suitable glidants can be used in the compositions which form the compartments. Preferred glidants are selected from the group consisting of colloidal silica, hydrophobic colloidal silica and magnesium trisilicate, such as talcum, particularly preferred glidants are selected from the group consisting of colloidal silica and hydrophobic colloidal silica.

The pharmaceutical composition according to the invention is preferably a dosage form, preferably a dosage form that is in a solid form, such as tablets, capsules (soft or hard capsules), caplets, lozenges, and sachets. A dosage form according to the present invention is preferably in the form of a tablet. Further preferred the dosage form, preferably the tablet, has at least one layer, preferably at least two layers, further preferred at least three layers. In a further preferred embodiment, the dosage form according to the present invention has one layer, preferably two layers or three layers.

The present invention also relates to a pharmaceutical composition, preferably a pharmaceutical dosage form, comprising at least one compartment, wherein the compartment contains an extended release composition comprising metformin or a pharmaceutically acceptable salt thereof and sitagliptin or a pharmaceutically acceptable salt thereof and wherein the pharmaceutical composition comprises at least one matrix agent. In a preferred embodiment, the amount of matrix agent(s) is in the range of 15-40 wt.-%. Preferably, the extended release composition contains at least one matrix agent as defined above. Furthermore, the pharmaceutical composition or dosage form might additionally comprise one or more excipients as defined above, as well as an outer API-free coating as described herein.

The present invention also relates to a process for preparing the pharmaceutical compositions according to the invention.

Thus, the present invention relates to a process for preparing dosage forms comprising metformin or a pharmaceutically acceptable salt thereof and sitagliptin or a pharmaceutically acceptable salt thereof, the process comprising the steps of:

a) providing one composition containing metformin or a pharmaceutically acceptable salt, and, optionally, also sitagliptin or a pharmaceutically acceptable salt, and b) providing a further composition containing sitagliptin or a pharmaceutically acceptable salt, and, optionally, also metformin or a pharmaceutically acceptable salt, and c) combining the compositions to form compartments, wherein at least one of the compartments represents an extended release composition and wherein the compositions of step a) and b) are not applied in a coating process. In a further preferred embodiment, the extended release compartment comprising metformin contains a matrix agent in an amount in the range of 15-40 wt.-%, and the extended release compartment comprising sitagliptin or a pharmaceutically acceptable salt thereof contains a matrix agent in an amount in the range of 15-60 wt.-%, further preferred 25-60 wt.-%. Preferably, the compartments are combined so that they are in direct contact with each other (i.e. side by side compartments are formed) or so that they are separated by an isolating layer.

Further preferred, sitagliptin is not dispersed in water during the process (as it would e.g. be the case during the preparation of a coating). With regard to the term "are in direct contact", reference is made to the specification above, as well as with regard to further amounts of the respective matrix agent/s. The compartments being in direct contact with each other offer the advantage that the process according to the present invention is improved in that the process is faster and cheaper compared to conventional processes comprising the formation of a layer that is between the respective compartments containing the API. Preferably process step c) is carried out in absence of any solvent; preferably process step c) involves the use of compression.

In the process steps a) and b), the compositions which form the compartment/s are prepared. The compositions comprise metformin and/or sitagliptin and optional further API(s), matrix agents and one or more excipients. Preferably, the excipients are selected from the group consisting of binding agents, fillers, filler-binder, disintegrants (only for immediate release compartments), lubricants, glidants, flavourings and colouring agents. Preferred excipients and matrix agents are described above. The compositions can be prepared by using suitable, well known methods such as mixing, high shear mixing, blending, sieving, granulating, lyophilization or milling of the ingredients. Preferably, the compositions are prepared by using a method which is suitable for use of the compositions in a subsequent compression step.

In a preferred embodiment, the preparation of the composition provided in step a) comprises a wet granulation step, and the preparation of the composition of step b) comprises a mixing step and/or granulation step. In a further embodiment, if a composition contains sitagliptin and metformin, the preparation of said composition comprises a granulation step. If a granulation step is comprised, a granulation liquid is used.

In a preferred embodiment, process step c) involves the use of compression. If an extended release compartment is prepared, a matrix agent is added to the composition and no disintegrant is added. If an immediate release compartment is prepared, a disintegrant is added and no matrix agent is added to the composition.

Preferably the compositions which form the compartments are pressed into the final dosage form like tablets. Further preferred a compression process is applied. Preferably, the (different) composition/s of the pharmaceutical composition pressed onto each other Furthermore, compression is the faster and more cost effective compared to coating process (way of tablet preparation). In order to carry out compression, preferably a tablet press capable of compressing multilayered, particular bilayered, tablets is used. Such a tablet press can be any tablet press that fulfils the above criteria, preferably a Riva bilayered tablet press is used. For preparing a tablet according to the present invention, the first and second compositions may be compressed in a bilayered tablet press in a well known bilayer tabletting mode.

Preferably, the process is carried out in order that each of the compartments constitutes a layer. Preferably, the dosage form is a tablet, preferably a bilayer or trilayer tablet, which consists of two or three separate compartments, each of which constitutes a layer.

The present invention also relates to a dosage form, obtained according to a process according to the present invention.

Furthermore, the present invention refers to the use of a dosage form according to any of the preceding items, for the treatment of diabetes.

After the compartments have been formed in process step c), an API-free outer coating can be applied. Such outer coatings can e.g. be functional coatings such as film coatings. Further possible outer coatings are for instance coatings that improve the palatability or smoothness/gliding ability/sliding ability of the dosage form. Such optional outer coating/s can comprise one or more of the excipients as described above.

It is possible that the process is carried out in the presence of air. This means that it is not necessary to carry out the process in inert atmosphere The process for preparing a pharmaceutical composition or dosage form having at least one compartment comprising an extended release composition comprising metformin and sitagliptin can be prepared by the process as described above, wherein in step a) a composition comprising both APIs and a matrix agent is provided and step b) is optional. In a further preferred embodiment, process step c) involves a compression step.

The following examples illustrate the process of the present invention and are not intended to limit the scope of the invention set forth in the claims appended hereto.

DESCRIPTION OF THE FIGURES

FIG. 1 shows the percentage of sitagliptin dissolved from formulations described in Examples 1-4, tested using App. 2 at 100 rpm in phosphate buffer medium pH 6.8.

FIG. 2 shows the percentage of metformin dissolved from formulations described in Examples 5-9, tested using App. 2; 100 rpm in phosphate buffer medium pH 6.8.

FIG. 3 shows the percentage of sitagliptin and metformin dissolved from formulation described in Example 10, tested using App. 2; 100 rpm in phosphate buffer medium pH 6.8.

FIG. 4 shows the percentage of sitagliptin and metformin dissolved from formulation described in Example 11, tested using App. 2; 100 rpm in phosphate buffer medium pH 6.8.

FIG. 5 shows the percentage of sitagliptin and metformin dissolved from formulation described in Example 12, tested using App. 2; 100 rpm in phosphate buffer medium pH 6.8.

FIG. 6 shows the percentage of sitagliptin and metformin dissolved from formulation described in Example 13, tested using App. 2; 100 rpm in phosphate buffer medium pH 6.8.

FIG. 7 shows the percentage of sitagliptin and metformin dissolved from formulation described in Example 14, tested using App. 2; 100 rpm in phosphate buffer medium pH 6.8.

FIG. 8 shows the percentage of sitagliptin and metformin dissolved from formulation described in Example 15, tested using App. 2; 100 rpm in phosphate buffer medium pH 6.8.

FIG. 9 shows the percentage of sitagliptin and metformin dissolved from formulation described in Example 16, tested using App. 2; 100 rpm in phosphate buffer medium pH 6.8.

FIG. 10 shows the percentage of sitagliptin and metformin dissolved from formulation described in Example 17, tested using App. 2; 100 rpm in phosphate buffer medium pH 6.8.

FIG. 11 shows the percentage of sitagliptin and metformin dissolved from formulation described in Example 18, tested using App. 2; 100 rpm in phosphate buffer medium pH 6.8.

FIG. 12 shows the percentage of sitagliptin and metformin dissolved from formulation described in Example 19, tested using App. 2; 100 rpm in phosphate buffer medium pH 6.8.

FIG. 13 shows the percentage of sitagliptin and metformin dissolved from formulation described in Example 20, tested using App. 2; 100 rpm in phosphate buffer medium pH 6.8.

EXAMPLES

Comparative Example 1

Sitagliptin Immediate Release Formulation—Formulation 001S

| Ingredient | Function | amount per tablet (mg) | portion (%) |
|---|---|---|---|
| Sitagliptin phosphate monohydrate | Active | 128.50 | 42.83 |
| Anhydrous dibasic calcium phosphate | Filler | 80.00 | 26.67 |
| Microcrystalline cellulose | Filler/binder | 82.50 | 27.50 |
| Croscarmellose sodium | Disintegrant | 6.00 | 2.00 |
| Magnesium stearate | Lubricant | 3.00 | 1.00 |
| | | 300.00 | 100.00 |

*equivalent to 100 mg of free base anhydrate

Sitagliptin phosphate monohydrate is mixed with anhydrous dibasic calcium phosphate, microcrystalline cellulose and croscarmellose sodium and sieved through an appropriate sieve. Sieved magnesium stearate is added and the composition blended for short period of time.

The blend is compressed into a bilayer tablet as disclosed in Examples 10, 11, 13, 14 and 16.

Comparative Example 2

Sitagliptin Extended Release Formulation Comprising a Hydrophilic Matrix Agent—Formulation 002S

| Ingredient | Function | amount per tablet (mg) | portion (%) |
|---|---|---|---|
| Sitagliptin phosphate monohydrate | Active | 128.50 | 42.83 |
| Hydroxypropylmethylcellulose methocel K100M premium | Rate controlling polymer | 120.00 | 40.00 |
| Microcrystalline cellulose | Filler/binder | 48.50 | 16.17 |
| Magnesium stearate | Lubricant | 3.00 | 1.00 |
| | | 300.00 | 100.00 |

*equivalent to 100 mg of free base anhydrate

Sitagliptin phosphate monohydrate, HPMC and microcrystalline cellulose are homogenously blended and sieved through appropriate sieve. Sieved magnesium stearate is added and blended for a short period of time.

The blend is compressed into a bilayer tablet as disclosed in Example 12.

Moreover, the tablet blend is compressed into extended release sitagliptin tablets, 300 mg.

Comparative Example 3

Sitagliptin Extended Release Formulation Comprising a Lipophilic Matrix Agent—Formulation 003S

| Ingredient | Function | amount per tablet (mg) | portion (%) |
|---|---|---|---|
| Sitagliptin phosphate monohydrate | Active | 128.50 | 42.83 |
| Hydrogenated castor oil | Lipophilic matrix agent | 120.00 | 40.00 |
| Microcrystalline cellulose | Filler/binder | 48.50 | 16.17 |
| Magnesium stearate | Lubricant | 3.00 | 1.00 |
| | | 300.00 | 100.00 |

*equivalent to 100 mg of free base anhydrate

Sitagliptin phosphate monohydrate, hydrogenated castor oil and microcrystalline cellulose are homogenously blended and sieved through an appropriate sieve. Sieved magnesium stearate is added and blended for short period of time.

The blend is compressed into a bilayer tablet as disclosed in Example 15.

Moreover, the tablet blend is compressed into extended release sitagliptin tablets, 300 mg.

Example 4

Sitagliptin Extended Release Formulation Comprising an Inert Matrix Agent—004S

| Ingredient | Function | amount per tablet (mg) | portion (%) |
|---|---|---|---|
| Sitagliptin phosphate monohydrate | Active | 128.50 | 42.83 |
| Ethylcellulose | Inert matrix agent | 120.00 | 40.00 |
| Microcrystalline cellulose | Filler/binder | 48.50 | 16.17 |
| Magnesium stearate | Lubricant | 3.00 | 1.00 |
| | | 300.00 | 100.00 |

*equivalent to 100 mg of free base anhydrate

Sitagliptin phosphate monohydrate, ethylcellulose and microcrystalline cellulose are homogenously blended and sieved through an appropriate sieve. Sieved magnesium stearate is added and blended for short period of time.

The blend is compressed into a bilayer tablet as disclosed in Example 17.

Moreover, the tablet blend is compressed into extended release sitagliptin tablets, 300 mg.

Dissolution profiles for Examples 1-4 are presented in FIG. 1.

Example 5

Metformin Extended Release Formulation Comprising a Hydrophilic Matrix Agent—Formulation 001M

| Ingredient | Function | amount per tablet (mg) | portion (%) |
|---|---|---|---|
| Metformin hydrochloride | Active | 1000.000 | 70.42 |
| Hydroxypropylmethylcellulose Methocel K100M Premium | Hydrophilic matrix agent | 350.000 | 24.65 |
| Demineralized water | Granulation liquid | 500.000 | — |
| Microcrystalline cellulose | Filler/binder | 62.900 | 4.43 |
| Magnesium stearate | Lubricant | 7.100 | 0.50 |
| Total | | 1420.000 | 100.00 |

* removed during the process

Metformin hydrochloride is screened through 1 mm sieve. Screened metformin hydrochloride and hydroxypropylmethylcellulose are granulated in fluid bed granulator with demineralized water and dried in the same device. Dried granulate is screened through 1 mm sieve. Obtained granulate and microcrystalline cellulose are homogenously blended in a bin blender. Pre-sieved magnesium stearate is added to the obtained blend and blended in a bin blender so that the final blend is obtained.

The final blend is compressed into a bilayer tablet as disclosed in Example 10.

Example 6

Metformin Extended Release Formulation Comprising a Hydrophilic Matrix Agent—Formulation 002M

| Ingredient | Function | amount per tablet (mg) | portion (%) |
|---|---|---|---|
| Metformin hydrochloride | Active | 1000.000 | 66.67 |
| Povidone | Binder | 75.00 | 5.00 |
| Demineralized water* | Granulation liquid vehicle | 550.000 | — |
| Microcrystalline cellulose | Filler/binder | 67.500 | 4.50 |
| Hydroxypropylmethylcellulose Methocel K100M Premium | Hydrophilic matrix agent | 350.000 | 23.33 |
| Magnesium stearate | Lubricant | 7.500 | 0.50 |
| Total | | 1500.000 | 100.00 |

*removed during the process

Metformin hydrochloride is screened through 1 mm sieve. Screened metformin hydrochloride is granulated in a fluid bed granulator with a solution of povidone in demineralized water and dried in the same device. The dried granulate is screened through 1 mm sieve. The obtained granulate, microcrystalline cellulose and hydroxypropylmethylcellulose are homogenously blended in a bin blender. Pre-sieved magnesium stearate is added to the obtained blend and blended in a bin blender so that the final blend is obtained. The final blend is compressed into a bilayer tablet as disclosed in Examples 11 in 12.

Example 7

Metformin Extended Release Formulation Comprising a Hydrophilic Matrix Agent—Formulation 003M

| Ingredient | Function | amount per tablet (mg) | portion (%) |
|---|---|---|---|
| Metformin hydrochloride | Active | 1000.000 | 66.67 |
| Povidone | Binder | 75.00 | 5.00 |
| Demineralized water* | Granulation liquid vehicle | 550.000 | — |
| Microcrystalline cellulose | Filler/binder | 67.500 | 4.50 |
| Hydroxypropyl cellulose Klucel MXF | Hydrophilic matrix agent | 350.000 | 23.33 |
| Magnesium stearate | Lubricant | 7.500 | 0.50 |
| Total | | 1500.000 | 100.00 |

*removed during the process

Metformin hydrochloride is screened through a 1 mm sieve. Screened metformin hydrochloride is granulated in a fluid bed granulator with a solution of povidone in demineralized water and dried in the same device. The dried granulate is screened through a 1 mm sieve. The obtained granulate, microcrystalline cellulose and hydroxypropylcellulose are homogenously blended in a bin blender. Pre-sieved magnesium stearate is added to the obtained blend and blended in a bin blender so that the final blend is obtained.

The final blend is compressed into a bilayer tablet as disclosed in Examples 13.

Example 8

Metformin Extended Release Formulation Comprising a Lipophilic Matrix Agent—Formulation 004M

| Ingredient | Function | amount per tablet (mg) | portion (%) |
|---|---|---|---|
| Metformin hydrochloride | Active | 1000.000 | 66.67 |
| Povidone | Binder | 75.00 | 5.00 |
| Demineralized water* | Granulation liquid vehicle | 550.000 | — |
| Microcrystalline cellulose | Filler/binder | 67.500 | 4.50 |
| Hydroxypropyl Castor Oil | Lipophilic matrix agent | 350.000 | 23.33 |
| Magnesium stearate | Lubricant | 7.500 | 0.50 |
| Total | | 1500.000 | 100.00 |

*removed during the process

Metformin hydrochloride is screened through a 1 mm sieve. Screened metformin hydrochloride is granulated in fluid bed granulator with the solution of povidone in demineralized water and dried in the same device. The dried granulate is screened through a 1 mm sieve. The obtained granulate, microcrystalline cellulose and hydrogenated castor oil are homogenously blended in a bin blender. Pre-sieved magnesium stearate is added to the obtained blend and blended in a bin blender so that the final blend is obtained. The final blend is compressed into a bilayer tablet as disclosed in Examples 14 and 15.

Example 9

Metformin Extended Release Formulation Comprising an Inert Matrix Agent—Formulation 005M

| Ingredient | Function | amount per tablet (mg) | portion (%) |
|---|---|---|---|
| Metformin hydrochloride | Active | 1000.000 | 66.67 |
| Povidone | Binder | 75.00 | 5.00 |
| Demineralized water* | Granulation liquid vehicle | 550.000 | — |
| Microcrystalline cellulose | Filler/binder | 67.500 | 4.50 |
| Ethyllcellulose Ethocel 10 FT Premium | Inert matrix agent | 350.000 | 23.33 |
| Magnesium stearate | Lubricant | 7.500 | 0.50 |
| Total | | 1500.000 | 100.00 |

*removed during the process

Metformin hydrochloride is screened through a 1 mm sieve. Screened metformin hydrochloride is granulated in a fluid bed granulator with a solution of povidone in demineralized water and dried in the same device. Dried granulate is screened through a 1 mm sieve. The obtained granulate, microcrystalline cellulose and ethylcellulose are homogenously blended in a bin blender. Pre-sieved magnesium stearate is added to the obtained blend and blended in bin blender so that the final blend is obtained. The final blend is compressed into a bilayer tablet as disclosed in Examples 16 and 17.

Dissolution profiles for Examples 5-9 are presented in FIG. 2.

Example 10

Bilayer Tablets Formulation 001N/2-IR Containing as a First Layer an Extended Release Formulation of Metformin Comprising a Hydrophilic Matrix Agent—Formulation 001M Disclosed in Example 5 and as a Second Layer an Immediate Release Formulation of Sitagliptin—Formulation 001S Disclosed in Example 1

| Ingredient | Layer | Function | amount per tablet (mg) |
|---|---|---|---|
| final blend 001M | first layer | extended release formulation of metformin comprising hydrophilic matrix agent | 1420.000 |
| final blend 001S | second layer | immediate release formulation of sitagliptin | 300.000 |
| Total bilayer tablet | | | 1720.000 |

The first and the second layer according to the composition in the table above are compressed into bilayer tablets.

Example 11

Bilayer Tablets—Formulation 002N/2-IR Containing as a First Layer an Extended Release Formulation of Metformin Comprising a Hydrophilic Matrix Agent—Formulation 002M Disclosed in Example 6 and as a Second Layer an Immediate Release Formulation of Sitagliptin—Formulation 001S Disclosed in Example 1

| Ingredient | Layer | Function | amount per tablet (mg) |
|---|---|---|---|
| final blend 002M | first layer | extended release formulation of metformin comprising hydrophilic matrix agent | 1500.000 |
| final blend 001S | second layer | immediate release formulation of sitagliptin | 300.000 |
| Total bilayer tablet | | | 1800.000 |

The first and the second layer according to the composition in the table above are compressed into bilayer tablets.

Example 12

Bilayer Tablets—Formulation 002N/2-XR Containing as a First Layer an Extended Release Formulation of Metformin Comprising a Hydrophilic Matrix Agent—Formulation 002M Disclosed in Example 6 and as a Second Layer an Extended Release Formulation of Sitagliptin Comprising Hydrophilic Matrix—Formulation 002S Disclosed in Example 2

| Ingredient | Layer | Function | amount per tablet (mg) |
|---|---|---|---|
| final blend 002M | first layer | extended release formulation of metformin comprising hydrophilic matrix agent | 1500.000 |
| final blend 002S | second layer | extended release formulation of sitagliptin comprising hydrophilic matrix | 300.000 |
| Total bilayer tablet | | | 1800.000 |

Example 13

Bilayer Tablets—Formulation 003N/2-IR Containing as a First Layer an Extended Release Formulation of Metformin Comprising a Hydrophilic Matrix Agent—Formulation 003M Disclosed in Example 7 and as a Second Layer an Immediate Release Formulation of Sitagliptin—Formulation 001S Disclosed in Example 1

| Ingredient | Layer | Function | amount per tablet (mg) |
|---|---|---|---|
| final blend 003M | first layer | extended release formulation of metformin comprising hydrophilic matrix agent | 1500.000 |
| final blend 001S | second layer | immediate release formulation of sitagliptin | 300.000 |
| Total bilayer tablet | | | 1800.000 |

The first and the second layer according to the compositions in the table above are compressed into bilayer tablets.

Example 14

Bilayer Tablets—Formulation 004N/2-IR Containing as a First Layer an Extended Release Formulation of Metformin Comprising a Lipophilic Matrix Agent—Formulation 004M Disclosed in Example 8 and as a Second Layer an Immediate Release Formulation of Sitagliptin—Formulation 001S Disclosed in Example 1

| Ingredient | Layer | Function | amount per tablet (mg) |
|---|---|---|---|
| final blend 004M | first layer | extended release formulation of metformin comprising lipophilic matrix agent | 1500.000 |
| final blend 001S | second layer | immediate release formulation of sitagliptin | 300.000 |
| Total bilayer tablet | | | 1800.000 |

The first and the second layer according to the compositions in the table above are compressed into bilayer tablets.

Example 15

Bilayer Tablets—Formulation 004N/2-XR Containing as a First Layer an Extended Release Formulation of Metformin Comprising a Lipophilic Matrix Agent—Formulation 004M Disclosed in Example 8 and as a Second Layer an Extended Release Formulation of Sitagliptin Comprising a Lipophilic Matrix—Formulation 003S Disclosed in Example 3

| Ingredient | Layer | Function | amount per tablet (mg) |
|---|---|---|---|
| final blend 004M | first layer | extended release formulation of metformin comprising lipophilic matrix agent | 1500.000 |
| final blend 003S | second layer | extended release formulation of sitagliptin comprising lipophilic matrix | 300.000 |
| Total bilayer tablet | | | 1800.000 |

The first and the second layer according to the compositions in the table above are compressed into bilayer tablets.

Example 16

Bilayer Tablets—Formulation 005N/2-IR Containing as a First Layer an Extended Release Formulation of Metformin Comprising an Inert Matrix Agent—Formulation 005M Disclosed in Example 9 and as a Second Layer an Immediate Release Formulation of Sitagliptin—Formulation 001S Disclosed in Example 1

| Ingredient | Layer | Function | amount per tablet (mg) |
|---|---|---|---|
| final blend 005M | first layer | extended release formulation of metformin comprising inert matrix agent | 1500.000 |
| final blend 001S | second layer | immediate release formulation of sitagliptin | 300.000 |
| Total bilayer tablet | | | 1800.000 |

The first and the second layer according to the compositions in the table above are compressed into bilayer tablets.

Example 17

Bilayer Tablets—Formulation 005N/2-XR Containing as a First Layer an Extended Release Formulation of Metformin Comprising an Inert Matrix Agent—Formulation 005M Disclosed in Example 9 and as a Second Layer Extended Release Formulation of Sitagliptin Comprising an Inert Matrix—Formulation 004S Disclosed in Example 4

| Ingredient | Layer | Function | amount per tablet (mg) |
|---|---|---|---|
| final blend 005M | first layer | extended release formulation of metformin comprising inert matrix agent | 1500.000 |
| final blend 004S | second layer | extended release formulation of sitagliptin comprising inert matrix | 300.000 |
| Total bilayer tablet | | | 1800.000 |

The first and the second layer according to the compositions in the table above are compressed into bilayer tablets.

Example 18

Extended Release Formulation of a Combination of Metformin and Sitagliptin Comprising a Hydrophilic Matrix Agent—Formulation 007N

| Ingredient | Function | amount per tablet (mg) | portion (%) |
|---|---|---|---|
| Sitagliptin phosphate monohydrate | Active | 64.250 | 3.97 |
| Metformin hydrochloride | Active | 1000.000 | 61.73 |
| Povidone | Binder | 92.400 | 5.70 |
| Demineralized water* | Granulation liquid vehicle | 677.600 | — |
| Microcrystalline cellulose | Filler/binder | 105.250 | 6.50 |
| Hydroxypropylmethylcellulose methocel k100m premium | Hydrophilic matrix agent | 350.000 | 21.60 |
| Magnesium stearate | Lubricant | 8.100 | 0.50 |
| Total | | 1620.000 | 100.00 |

Metformin hydrochloride is screened through a 1 mm sieve. Screened metformin hydrochloride and sitagliptin phosphate monohydrate are granulated in a fluid bed granulator with a solution of povidone in demineralized water and dried in the same device. The dried granulate is screened through a 1 mm sieve. The obtained granulate, microcrystalline cellulose and hydroxypropylmethylcellulose are homogenously blended in a bin blender. Pre-sieved magnesium stearate is added to the obtained blend and blended in a bin blender so that final blend is obtained.

The final blend is compressed into monolayer tablets.

Example 19

Extended Release Formulation of Combination of Metformin and Sitagliptin Comprising a Lipophilic Matrix Agent—Formulation 008N

| Ingredient | Function | amount per tablet (mg) | portion (%) |
|---|---|---|---|
| Sitagliptin phosphate monohydrate | Active | 64.250 | 3.97 |
| Metformin hydrochloride | Active | 1000.000 | 61.73 |
| Povidone | Binder | 92.400 | 5.70 |
| Demineralized water* | Granulation liquid vehicle | 677.600 | — |
| Microcrystalline cellulose | Filler/binder | 105.250 | 6.50 |
| Hydrogenated Castor oil methocel k100m premium | Lipophilic matrix agent | 350.000 | 21.60 |
| Magnesium stearate | Lubricant | 8.100 | 0.50 |
| Total | | 1620.000 | 100.00 |

Metformin hydrochloride is screened through a 1 mm sieve. Screened metformin hydrochloride and sitagliptin phosphate monohydrate are granulated in a fluid bed granulator with the solution of povidone in demineralized water and dried in the same device. Dried granulate is screened through a 1 mm sieve. The obtained granulate, microcrystalline cellulose and hydrogenated castor oil are homogenously blended in a bin blender. Pre-sieved magnesium stearate is added to the obtained blend and blended in a bin blender so that the final blend is obtained.

The final blend is compressed into monolayer tablets.

Example 20

Extended Release Formulation of Combination of Metformin and Sitagliptin Comprising an Inert Matrix Agent—Formulation 009N

| Ingredient | Function | amount per tablet (mg) | portion (%) |
|---|---|---|---|
| Sitagliptin phosphate monohydrate | Active | 64.250 | 3.97 |
| Metformin hydrochloride | Active | 1000.000 | 61.73 |
| Povidone | Binder | 92.400 | 5.70 |
| Demineralized water* | Granulation liquid vehicle | 677.600 | — |
| Microcrystalline cellulose | Filler/binder | 105.250 | 6.50 |
| Ethylcellulose Ethocel 10 FT Premium | Inert matrix agent | 350.000 | 21.60 |
| Magnesium stearate | Lubricant | 8.100 | 0.50 |
| Total | | 1620.000 | 100.00 |

Metformin hydrochloride is screened through a 1 mm sieve. Screened metformin hydrochloride and sitagliptin phosphate monohydrate are granulated in fluid bed granulator with the solution of povidone in demineralized water and dried in the same device. Dried granulate is screened through a 1 mm sieve. The obtained granulate, microcrystalline cellulose and ethylcellulose are homogenously blended in a bin blender. Pre-sieved magnesium stearate is added to the obtained blend and blended in a bin blender so that the final blend is obtained.

The final blend is compressed into monolayer tablets.

The invention claimed is:

1. A pharmaceutical composition comprising at least two separate compartments, wherein one compartment contains a composition comprising metformin or a pharmaceutically acceptable salt thereof and wherein another compartment contains a composition comprising sitagliptin or a pharmaceutically acceptable salt thereof, wherein at least one of the compartments is an extended release composition, wherein neither of said two compartments is a coating, wherein an extended release compartment comprising metformin or a pharmaceutically acceptable salt thereof contains a matrix agent in an amount in the range of 10-40 wt.-%, and wherein an extended release compartment comprising sitagliptin or a pharmaceutically acceptable salt thereof contains a matrix agent in an amount in the range of 15-60 wt.-%.

2. The pharmaceutical composition according to claim 1, wherein each of the compartments constitutes a layer.

3. The pharmaceutical composition according to claim wherein the pharmaceutical composition is a dosage form.

4. The pharmaceutical composition according to claim 1, wherein the other compartment also is an extended release composition.

5. The pharmaceutical composition according to claim 1, wherein the extended release composition comprises at least one matrix agent selected from the group consisting of hydrophilic agents, lipophilic agents and inert matrix agents, wherein
   the hydrophilic matrix agents are selected from the group consisting of cellulose derivatives; noncellulose polysaccharides; polyvinylpyrrolidone; polyvinylacetate polymers and copolymers; acrylic acid polymers and copolymers and polyethylene oxide and mixtures thereof;
   the lipophilic matrix agents are selected from the group consisting of waxes; fatty acids and alcohols; and mixtures thereof; and
   the inert matrix agents are thermoplastic polymers, which are insoluble and indigestible in the gastrointestinal fluids.

6. The pharmaceutical composition according to claim 1, wherein the composition contains one or more additional excipients, which are selected from the group consisting of binding agents, fillers, filler-binder, disintegrants, lubricants, glidants, flavourings and colouring agents.

7. A process for preparing dosage forms comprising metformin or a pharmaceutically acceptable salt thereof and sitagliptin or a pharmaceutically acceptable salt thereof, the process comprising the steps of:
   a) providing one composition containing metformin or a pharmaceutically acceptable salt thereof and optionally also sitagliptin,
   b) providing a further composition containing sitagliptin or a pharmaceutically acceptable salt thereof and optionally also metformin, and
   c) combining the compositions to form compartments,
   wherein at least one of the compartments is an extended release composition, and wherein the compositions of step (a) and (b) are not applied in a coating process and wherein an extended release compartment comprising metformin or a pharmaceutically acceptable salt thereof contains a matrix agent in an amount in the range of 10-40 wt.-%, and wherein an extended release compartment comprising sitagliptin or a pharmaceutically acceptable salt thereof contains a matrix agent in an amount in the range of 15-60 wt.-%.

8. The process according to claim 7, wherein the dosage form is a tablet and wherein each of the compartments a layer.

9. The process according to claim 7, wherein the preparation of the composition provided in step a) comprises a granulation step, and wherein the preparation of the composition of step b) comprises a mixing step.

10. The process according to claim 7, wherein process step c) involves the use of compression.

11. The process according to claim 7, wherein matrix agent(s) and optional one or more further excipients are incorporated in the respective compositions.

12. A dosage form, obtained according to a process according to claim 7.

13. A method of treating diabetes, comprising administering to a subject in need thereof a therapeutically effective amount of the pharmaceutical dosage form according to claim 1.

* * * * *